United States Patent [19]

Kelly et al.

[11] Patent Number: 5,346,647

[45] Date of Patent: Sep. 13, 1994

[54] CYCLOHEXANE COMPOUNDS USED IN LIQUID CRYSTALLINE MIXTURES

[75] Inventors: Stephen Kelly, Möhlin, Switzerland; Frans Leenhouts, Achel, Belgium

[73] Assignee: Hoffmann-La Roche Inc., Nutley, N.J.

[21] Appl. No.: 166,603

[22] Filed: Dec. 13, 1993

Related U.S. Application Data

[63] Continuation of Ser. No. 943,375, Sep. 10, 1992, abandoned, which is a continuation of Ser. No. 554,636, Jul. 17, 1990, abandoned.

[30] Foreign Application Priority Data

Jul. 25, 1989 [CH] Switzerland ............... 2779/89
Apr. 10, 1990 [CH] Switzerland ............... 1239/90

[51] Int. Cl.$^5$ ............. C09K 19/30; C09K 19/34; C07D 239/02
[52] U.S. Cl. .................. 252/299.63; 252/299.01; 252/299.61; 252/299.62; 544/242; 544/298; 544/335; 546/192; 546/251; 359/103
[58] Field of Search ......... 252/299.01, 299.6, 299.61, 252/299.62, 299.63; 544/242, 298, 335; 359/103; 546/192, 251

[56] References Cited

U.S. PATENT DOCUMENTS

| | | | |
|---|---|---|---|
| 4,035,056 | 7/1977 | Coates et al. | 350/160 |
| 4,627,933 | 12/1986 | Eidenschink et al. | 252/299.6 |
| 4,676,604 | 6/1987 | Petrzilka | 350/350 R |
| 4,713,197 | 12/1987 | Eidenschink et al. | 252/299.61 |
| 4,886,620 | 12/1989 | Hopf et al. | 252/299.61 |
| 4,894,181 | 1/1990 | Praefcke et al. | 252/299.61 |
| 4,943,384 | 7/1990 | Sucrow et al. | 252/299.61 |
| 5,238,600 | 8/1993 | Kelly | 252/299.63 |

FOREIGN PATENT DOCUMENTS 0344557 of 1989 European Pat. Off. .

OTHER PUBLICATIONS

Poetsch, Kontakte (Darmstadt) 2, 15–28 (1988).

*Primary Examiner*—Shean Wu
*Attorney, Agent, or Firm*—George M. Gould; George W. Johnston

[57] ABSTRACT

Compounds of the formula

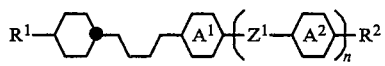

I wherein n stands for the number 0 or 1; $R^1$ denotes a group $R^3$ or $R^3$—$A^3$—$Z^2$— and $R^2$ denotes a group $R^4$ or $R^4$—$A^4$—$Z^3$—; ring $A^1$ is unsubstituted or halogen-, cyano- and/or methylsubstituted 1,4-phenylene in which optionally 1 CH group or 2 CH groups is/are replaced by nitrogen; $A^3$ $A^4$ and ring $A^2$ each independently represent unsubstituted or halogen-, cyano- and/or methyl-substituted 1,4-phenylene in which optionally 1 CH group or 2 CH groups is/are replaced by nitrogen or trans-1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,6-diyl or trans-decalin-2,6-diyl; $Z^1$, $Z^2$ and $Z^3$ each independently are a single covalent bond, —COO—, —OOC—, —CH$_2$O—, —OCH$_2$—, —CH$_2$CH$_2$—, —C|C—, —(CH$_2$)$_3$O—, —O(CH$_2$)$_3$—, —(CH$_2$)$_4$— or the trans form of —CH=CH—CH$_2$O— or —OCH$_2$—CH=CH—; $R^3$ and $R^4$ each independently denote halogen, cyano, —NCS, —CF$_3$, —OCF$_3$ or alkyl in which optionally one >CH—CH< is replaced by >C=C< and/or optionally one methylene group or two non-adjacent methylene groups is/are replaced by —O—, —COO— and/or —OOC— and/or optionally one methylene group is replaced by —CHX—; and X is halogen, cyano or methyl, as well as liquid crystalline mixtures which contain such compounds and their use for electro-optical purposes.

18 Claims, No Drawings

CYCLOHEXANE COMPOUNDS USED IN LIQUID CRYSTALLINE MIXTURES

This is a continuation of U.S. application Ser. No. 07/943,375, filed Sep. 10, 1992, now abandoned, which is a continuation of U.S. application Ser. No. 07/554,636, filed Jul. 17, 1990, now abandoned.

FIELD OF THE INVENTION

The present invention is concerned with novel (4-arylbutyl)cyclohexane derivatives, liquid crystalline mixtures which contain such compounds and their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), guest/host cells, TN cells ("twisted nematic") and STN cells ("super-twisted nematic") having a twisted nematic structure, SBE cells ("super birefringence effect"), phase change cells having a cholesteric-nematic phase transition and OMI cells ("optical mode interference"). The most common indicating devices are based on the Schadt-Helfrich effect and have a twisted nematic structure.

Further, electro-optical devices based on chiral tilted smectic liquid crystals have been proposed in Appl. Phys. Lett. 36, 899 (1980) and in Recent Developments in Condensed Matter Physics 4, 309 (1981). In such cases the ferroelectric properties of these materials are used. As the tilted smectic phases there are suitable, for example, smectic C, F, G, H, I and K phases. There are generally preferred smectic C phases which permit especially high response speeds. The chiral tilted phases are usually denoted by $S_C^*$ $S_F^*$ etc, with the asterisk indicating chirality.

The liquid crystal materials must have a good chemical and thermal stability and a high stability towards electric fields and electromagnetic radiation. Further, the liquid crystal materials should have low viscosity and in the cells should give short response times, low threshold potentials and a high contrast. Furthermore, at the usual operating temperatures they should have a suitable mesophase, for example a nematic, cholesteric or chiral tilted smectic phase. Further properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible. Besides the general interest in liquid crystal materials having a high optical anisotropy, there has recently been an increased interest in materials having a low optical anisotropy, especially for actively addressed liquid crystal indicators, for example, in the case of TFT applications (thin film transistor) in television sets. On the other hand, chiral tilted smectic liquid crystals should have a sufficiently high spontaneous polarization.

In order to optimize the properties, liquid crystals are generally used as mixtures of several components. It is therefore important that the components have a good miscibility with one another. Cholesteric mixtures can preferably consist of one or more optically active dopants and a nematic liquid crystal material and ferroelectric liquid crystals can preferably consist of one or more optically active dopants and a liquid crystal material having a tilted smectic phase.

DE-A-26 17 593 and DE-A-32 25 290 disclose liquid crystal components in which two or more rings can be linked via a bridging group having more than 2 chain atoms, for example via a —$(CH_2)_4$— group. Enantiotropic mesophases have, however, only been found for tetracyclic compounds (as well as for certain tricyclic compounds which, however, have an ester group in the bridging group) and the clearing points lie significantly lower than the case of corresponding compounds having 2 chain atoms in the bridging group or with directly linked rings.

SUMMARY OF THE INVENTION

The object of the present invention are the compounds of formula

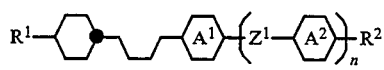

wherein n stands for the number 0 or 1: $R^1$ denotes a group $R^3$ or $R^3$—$A^3$—$Z^2$— and $R^2$ denotes a group $R^4$ or $R^4$—$A^4$—$Z^3$—; ring $A^1$ is unsubstituted or halogen, cyano and/or methylsubstituted 1,4-phenylene in which optionally 1 CH group or 2 CH groups is/are replaced by nitrogen; $A^3$, $A^4$ and ring $A^2$ each independently represent unsubstituted or halogen. cyano and/or methylsubstituted 1,4-phenylene in which optionally 1 CH group or 2 CH groups is/are replaced by nitrogen or trans-1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,6-diyl or trans-decalin-2,6-diyl; $Z^1$ $Z^2$ and $Z^3$ each independently are a single covalent bond, —COO—, —OOC—, —$CH_2O$—, —$OCH_2$—, —$CH_2CH_2$—, —C|C—, —$(CH_2)_3O$—. —$O(CH_2)_3$—, —$(CH_2)_4$— or the trans form of —CH=CH—$CH_2O$— or —$OCH_2$—CH=CH—; $R^3$ and $R^4$ each independently denote halogen, cyano, —NCS, —$CF_3$, —$OCF_3$ or alkyl in which optionally one >CH—CH< is replaced by —C=C< and/or optionally one methylene group or two non-adjacent methylene groups is/are replaced by —O—, —COO— and/or —OOC— and/or optionally one methylene group is replaced by —CHX—; and X is halogen, cyano or methyl.

DETAILED DESCRIPTION OF THE PREFERRED EMBODIMENTS

The present invention concerns compounds of formula

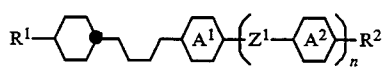

wherein n is 0 or 1; $R^1$ represents a group $R^3$ or $R^3$—$A^3$—$Z^2$—; $R^2$ is a group $R^4$ or $R^4$—$A^4$—$Z^3$—; ring $A^1$ represents unsubstituted 1,4-phenylene, 1,4-phenylene substituted with halogen, cyano, methyl or cyano and methyl, unsubstituted 1,4-phenylene having 1 CH or 2

CH groups replaced by nitrogen and 1,4-phenylene substituted with halogen, cyano, methyl, and cyano and methyl, unsubstituted 4-phenylene having 1 CH or 2 CH groups replaced by nitrogen and 1,4-phenylene substituted with halogen, cyano, methyl, and cyano and methyl and having 1 CH or 2 CH groups replaced by Nitrogen; $A^3$ $A^4$ and ring $A^2$ each independently represent 1,4-phenylene which is unsubstituted or substituted with halogen, cyano, methyl or cyano and methyl and the 1,4-phenylene optionally has 1CH or 2CH groups replaced by nitrogen or trans-1,4-cyclohexylene, trans-1,3-dioxane-2,5-diyl, 1-cyano-trans-1,4-cyclohexylene, bicyclo [2.2.2] octane-1,4-diyl, naphthalene-2,6-diyl, tetralin-2,6-diyl, and trans-decalin-2,6-diyl; $Z^1$, $Z^2$ and $Z^3$ each independently represent a single covalent bond, —COO—, —OOC—, —CH$_2$O—, —OCH$_2$—, —CH$_2$CH$_2$—, —C|C—, —(CH$_2$)$_3$O—, —O(CH$_2$)$_3$—, —(CH$_2$)$_4$— or a trans form of —CH=CH—CH$_2$O— or —OCH$_2$—CH=CH—; $R^3$ and $R^4$ each independently represent halogen, cyano, —NCS, —CF$_3$, —OCF$_3$, alkyl, alkyl having one >CH—CH< replaced by >C=C< alkyl having one methylene group or two non-adjacent methylene groups replaced by —O—, —COO—, —OOC— or —COO— and —OOC—, alkyl having one methylene group replaced by —CHX—, alkyl with one methylene group or two non-adjacent methylene groups being replaced by —O—, —COO—, —OOC— or —COO— and —OOC—, and one methylene group being replaced by —CHX—, alkyl having >CH—CH< replaced by >C=C< with one methylene group or two non-adjacent methylene groups being replaced by —O—, —COO—, —OOC— or —COO— and —OOC—, alkyl having one >CH—CH< replaced by >C=C< with one methylene group replaced by —CHX—, and alkyl having one >CH—CH< replaced by >C=C< with one methylene or two non-adjacent methylene groups being replaced by —O—, —COO—, —OOC— or —COO— and —OOC—, and one methylene group being replaced by —CHX—; and X represents halogen, cyano or methyl.

It has been surprisingly found that the compounds of formula I, which have a butane bridging group between a cyclohexane ring and an aromatic ring $A^1$, have a pronounced tendency to form liquid crystalline phases in spite of the high flexibility of the bridging group. The optically inactive compounds of formula I have for the most part a nematic, a smectic A and/or a tilted smectic (primarily $S_C$) phase and the optically active compounds of formula I have for the most part a cholesteric, a smectic A and/or a chiral tilted smectic (primarily $S_C*$) phase. These mesophase types are especially suitable for achieving nematic, cholesteric or chiral tilted smectic phases in liquid crystal mixtures. Compounds of formula which have a highly ordered smectic phase, for example, a smectic B phase, also have, however, a good miscibility with usual liquid crystal materials. The present intention accordingly provides a wide range of novel components and mixtures for the further optimization and modification of liquid crystal materials.

The compounds of formula I possess a high chemical stability and a high stability towards electric and magnetic fields. They are colourless, can be prepared readily and have a good solubility with one another and known liquid crystal materials. Further, they possess low viscosities and give short response times in indicating devices.

The properties of the compounds of formula I can be varied in wide ranges depending on the number and significance of the rings and of the substituents. For example, aromatic rings lead to higher values of the optical anisotropy and saturated rings lead to lower values of the optical anisotropy. An increase in the clearing point can be achieved, for example, by the influence of one or more additional rings. Polar end groups such as cyano, halogen, —NCS, —CF$_3$ or —OCF$_3$ and rings such as pyrimidine-2,5diyl, trans-1,3-dioxane-2,5-diyl etc. increase the dielectric anisotropy, rings such as pyridazine-3,6-diyl, 1-cyano-trans-1,4-cyclohexylene, 2,3-dicyano-1,4-phenylene etc. reduce the dielectric anisotropy and lateral halogen and cyano substituents contribute to the dielectric constants not only parallel to but also perpendicular to the longitudinal axis of the molecule, which can be utilized depending on the substitution pattern to increase or reduce the dielectric anisotropy. Further, the mesophase range can be modified, a possible tendency to form highly ordered smectic phases can be largely suppressed and frequently the solubility can also be improved by lateral substituents on one or more rings. Furthermore, the elastic properties, the threshold potentials, the response times, the mesophases etc. can be modified further by a C=C double bond in the side-chain.

The compounds in accordance with the invention therefore permit a further optimization of liquid crystal mixtures and a modification of the electro-optical properties in a wide range according to the desired properties.

The term "halogen" denotes in the scope of the present invention fluorine, chlorine, bromine or iodine, especially fluorine or chlorine.

The term "unsubstituted or halogen-, cyano- and/or methyl-substituted 1,4-phenylene in which optionally 1 CH group or 2 CH groups is/are replaced by nitrogen" embraces groups such as 1,4-phenylene, 2-fluoro-1,4-phenylene, 2,3-difluoro-1,4-phenylene, 2-chloro-1,4-phenylene, 2-bromo-1,4-phenylene, 2-cyano-1,4-phenylene, 2,3-dicyano-1,4-phenylene, 2-methyl-1,4-phenylene, pyridine-2,5-diyl, pyrazine-2,5-diyl, pyrimidine-2,5-diyl, pyridazine-3,6-diyl and the like. 1,4-phenylene, 2-fluoro-1,4-phenylene, 2,3-difluoro-1,4-phenylene, pyridine-2,5-diyl, pyrazine-2,5-diyl and pyrimidine-2,5-diyl are preferred groups.

The term "tetralin-2,6-diyl" denotes 1,2,3,4-tetrahydronaphthalene-2,6-diyl. The term "trans-decalin-2,6-diyl" embraces 2,6-disubstituted groups derived from trans-decahydronaphthalene, especially (4a$\alpha$H,8a$\beta$H)-decahydronaphthalene-2$\alpha$,6$\beta$-diyl.

The term "alkyl in which optionally one >CH—CH< is replaced by >C=C< and/or one methylene group or two non-adjacent methylene groups is/are replaced by —O—, —COO— and/or —OOC— and/or optionally one methylene group is replaced by —CHX—" embraces straight-chain and branched (optionally chiral) residues such as alkyl, 1E-alkenyl, 3E-alkenyl, 4-alkenyl, alkenyl having a terminal double bond, alkoxy, 2E-alkenyloxy, 3-alkenyloxy, alkenyloxy having a terminal double bond, alkoxyalkyl, alkenyloxyalkyl, alkoxycarbonyl, alkoxycarbonylalkoxy, alkanoyloxy, 1-haloalkyl, 2-haloalkyl, 2-haloalkoxy, 2-haloalkoxycarbonyl, 1-cyanoalkyl, 2-cyanoalkyl, 2-cyanoalkoxy, 2-cyanoalkoxycarbonyl, 1-methylalkyl, 2-methylalkyl, 1-methylalkoxy, 2-methylalkoxy, 2-methylalkoxycarbonyl and the like. Examples of preferred residues are methyl, ethyl, propyl, butyl, pentyl, hexyl, heptyl, octyl, nonyl, decyl, undecyl, dodecyl, 1-methylpropyl, 1-methylheptyl, 2-methylbutyl, 3- methylpentyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, 1-methylpropyloxy, 1-methylheptyloxy, 2-methylbutyloxy, 3-methylpentyloxy, allyloxy, 2E-butenyloxy, 2E-pentenyloxy, 2E-hexenyloxy, 2E-heptenyloxy, 3-butenyloxy, 3Z-pentenyloxy, 3Z-hexeny oxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, allyloxymethyl, methoxycarbonyl, ethoxycarbonyl, propyloxycarbonyl, 1-methylpropyloxycarbonyl, 1-(methoxycarbonyl)ethoxy, 1-(ethoxycarbonyl)ethoxy, acetoxy, propionyloxy, butyryloxy, 1-fluoropropyl, 1-fluoropentyl, 1-chloropropyl, 2-fluoropropyl, 2-fluoropentyl, 2-chloropropyl, 2-fluoropropyloxy, 2-fluorobutyloxy, 2-fluoropentyloxy, 2-fluorohexyloxy, 2-chloropropyloxy, 2-fluorobutyloxy, 2-fluoropropyloxycarbonyl, 2-fluorobutyloxycarbonyl, 2-fluoropentyloxycarbonyl, 2-fluoro-3-methylbutyloxycarbonyl, 2-fluoro-4-methylpentyloxycarbonyl, 2-chloropropyloxycarbonyl, 1-cyanopropyl, 1-cyanopentyl, 2-cyanopropyl, 2-cyanopentyl, 2-cyanopropyloxy, 2-cyanobutyloxy, 2-cyanopentyloxy, 2-cyanohexyloxy, 2-cyanopropyloxycarbonyl, 2-cyanobutyloxycarbonyl, 2-cyano-3-methylbutyloxycarbonyl, 2-cyano-4-methylpentyloxycarbonyl and the like.

Preferred compounds of formula I are the compounds of formulas wherein n, $R^1$, $R^2$, $Z^1$ and ring $A^2$ have the above significances and $X^1$ and $X^2$ each independently denote hydrogen, halogen, cyano or methyl.

In formulas I and I-1 to I-6 above ring $A^2$ preferably stands for unsubstituted 1,4-phenylene or 1,4-phenylene which is monosubstituted or 2,3-disubstituted with halogen, cyano and/or methyl, for trans-1,4-cyclohexylene, trans-1,3-dioxane-2,5-diyl, 1-cyano-trans-1,4-cyclohexylne, bicyclo[2.2.2]octane-1,4-diyl, naphthalene-2,6-diyl, tetralin-2,6-diyl, trans-decalin-2,6-diyl or in formulas I and I-1 also for pyridine-2,5-diyl, pyrimidine-2,5-diyl or pyrazine-2,5-diyl.

Preferably, $A^3$ and $A^4$ each independently stand for trans-1,4-cyclohexylene or for unsubstituted or halogen-, cyano- and/or methyl-substituted 1,4-phenylene, especially for trans-1,4-cyclohexylene.

Preferably, $Z^1$, $Z^2$ and $Z^3$ each stand for a single covalent bond or one of the groups $Z^1$, $Z^2$ and $Z^3$ (preferably $Z^1$) also stands for —COO—, —OOC—, —CH$_2$O—, —OCH$_2$—, —CH$_2$CH$_2$—, —C|C—, —(CH$_2$)$_3$O—, —O(CH$_2$)$_3$—, —(CH$_2$)$_4$— or the trans form of —CH=CH—CH$_2$O— or —OCH$_2$—CH=CH—.

The bicyclic and the tricyclic compounds of formulas I and I-1 to I-6 are preferred basic materials for liquid crystalline mixtures. In the bicyclic compounds n stands for the number O, $R^1$ stands for $R^3$ and $R^2$ stands for $R^4$. In the tricyclic compounds n stands for the number 1, $R^1$ stands for $R^3$ and $R^2$ stands for $R^4$ or n stands for the number O, $R^1$ stands for $R^3$—$A^3$—$Z^2$— and $R^2$ stands for $R^4$ or n stands for the number O, $R^1$ stands for $R^3$ and $R^2$ stands for $R^4$—$A^4$—$Z^3$—. Compounds having 4 or 5 rings are, however, preferred when high clearing points are desired (for example, for use as dopants for

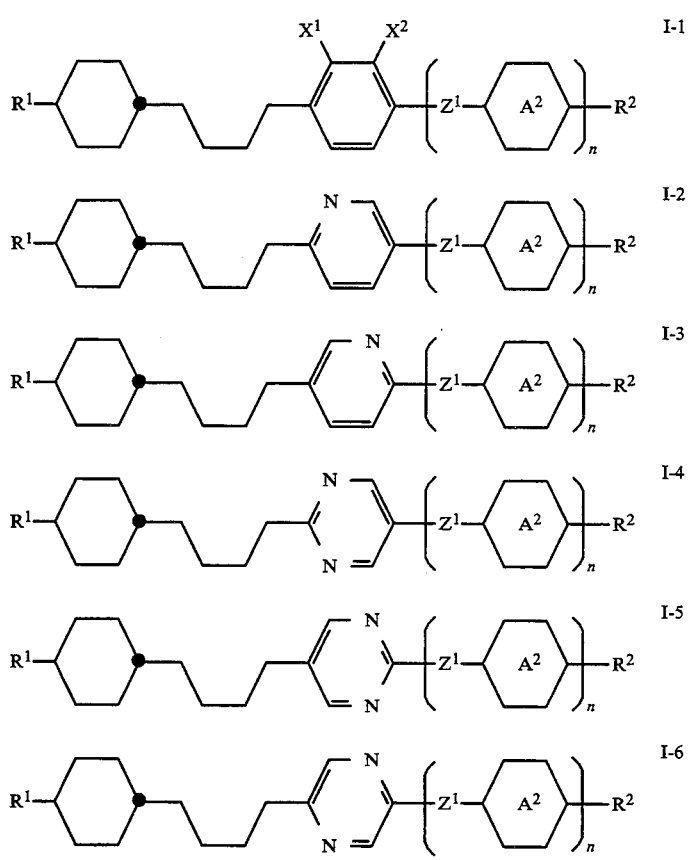

increasing the clearing point or as a stationary phase in gas chromatography).

Examples of especially preferred sub-groups of compounds of formula I are the compounds of the formula

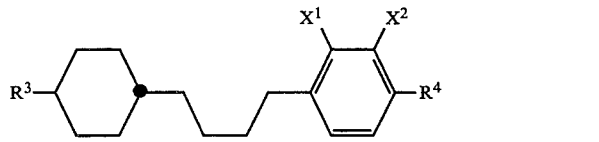
I-7

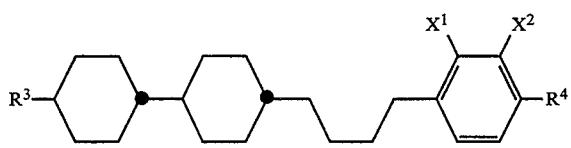
I-8

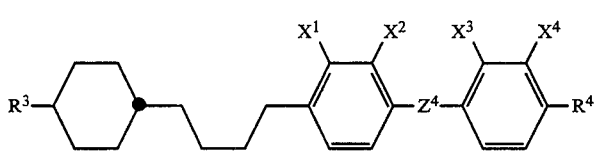
I-9

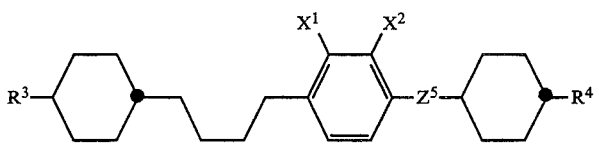
I-10

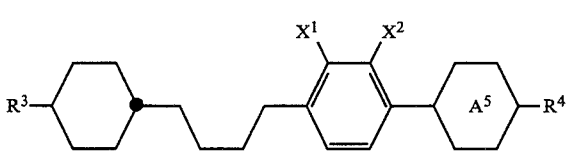
I-11

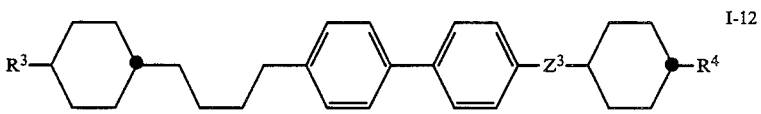
I-12

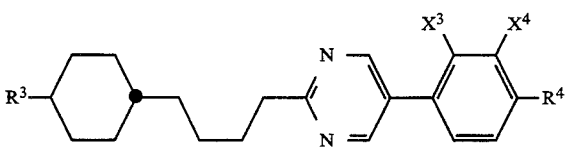
I-13

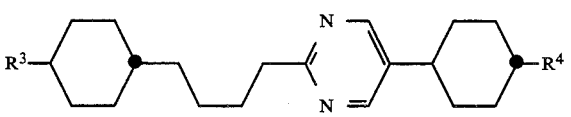
I-14

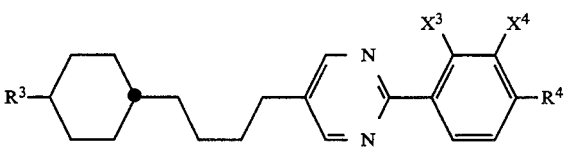
I-15

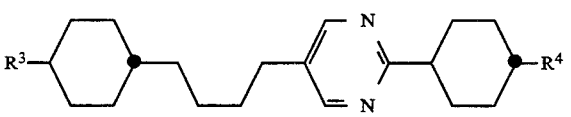
I-16 wherein $R^3$ $R^4$ and $Z^3$ have the above significances, $X^1$, $X^2$ $X^3$ and $X^4$ each independently denote hydrogen, halogen, cyano or methyl, $Z^4$ is a single covalent bond, —COO—, —OOC— or —C|C—; $Z^5$ denotes a single covalent bond, —OOC—, —OCH$_2$—, —CH$_2$CH$_2$—, —C|C—, —O(CH$_2$)$_3$—, —(CH$_2$)$_4$— or the trans form of —OCH$_2$—CH=CH—; and ring $A^5$ represents pyridine-2,5-diyl, pyrimidine-2,5-diyl, pyrazine-2,5-diyl, trans-1,3-dioxane-2,5-diyl, bicyclo[2.2.2]octane-1,4-diyl, naphthalene-2,6-diyl; tetralin-2,6-diyl or trans-decalin-2,6-diyl.

In general, there are preferred compounds of formula I without lateral substituents or with lateral fluorine substituents (preferably a maximum of one or two lateral fluorine substituents), that is, in formulas I-1, I-7 to I-11, I-13 and I-15 above the substituents $X^1$, $X^2$, $X^3$ and $X^4$ preferably stand for hydrogen or fluorine, especially for hydrogen or 1 or 2 of the substituents $X^1$, $X^2$, $X^3$ and $X^4$ also stands for fluorine. It will, however, be evident to a person skilled in the art that in place of fluorine there can also be used other halogen substituents especially chlorine, and that by lateral methyl substitution the solubility can frequently be improved or by cyano substituents a strong lateral dipole moment can be produced.

In formula 1-11 an optionally present pyridine ring, pyrimidine ring, pyrazine ring or 1,3-dioxane ring can be linked in the 2-position or in the 5-position with the benzene ring.

Preferably, a maximum of one of the residues $R^3$ and $R^4$ (preferably $R^4$) stands for halogen, cyano, —NCS, —CF$_3$ or —OCF$_3$, that is, preferably $R^3$ and $R^4$ each independently denote alkyl in which optionally one >CH—CH< is replaced by >C=C< and/or optionally one methylene group or two non-adjacent methylene groups is/are replaced by —O—, —COO— and/or —OOC— and/or optionally one methylene group is replaced by —CHX— or one of the residues $R^3$ and $R^4$ (preferably $R^4$) also denotes halogen, cyano, —NCS, —CF$_3$ or —OCF$_3$. A terminal halogen atom and the —NCS group are preferably present on an aromatic ring, especially a benzene, pyridine, pyrimidine or pyrazine ring.

$R^3$ and $R^4$ in formulas I and I-1 to 1-16 above each preferably have a maximum of about 18, especially a maximum of about 12, carbon atoms.

For nematic and cholesteric applications there are generally preferred short residues $R^3$ and $R^4$ (for example, residues with a maximum of 12, preferably a maximum of 7, carbon atoms) and preferably one of the residues can also be halogen, cyano, —NCS, —CF$_3$ or —OCF$_3$. For smectic applications (especially tilted smectic phases) there are generally preferred those compounds in which $R^3$ and $R^4$ each independently denote alkyl in which optionally one >CH—CH< is replaced by >C=C< and/or optionally one methylene group or two non-adjacent methylene groups is/are replaced by —O—, —COO— and/or —OOC— and/or optionally one methylene group is replaced by —CHX— and the sum of the carbon atoms in $R^3$ and $R^4$ together amounts to at least 10, preferably at least 12.

Preferred residues $R^3$ are alkyl, alkenyl, alkoxy, alkenyloxy, alkoxycarbonyl, alkenyloxycarbonyl, alkanoyloxy and alkenoyloxy, especially alkyl and alkenyl. Residues $R^3$ with up to 12 carbon atoms are generally especially preferred. Preferred residues are alkyl, alkenyl, alkoxy, alkenyloxy, alkoxycarbonyl, alkenyloxycarbonyl, alkanoyloxy and alkenoyloxy (especially alkyl, alkenyl, alkoxy and alkenyloxy) as well as halogen (especially fluorine and chlorine), cyano, —NCS, —CF$_3$ and —OCF$_3$. Residues $R^4$ with up to 12 carbon atoms are generally especially preferred.

Straight-chain residues $R^3$ and, respectively, $R^4$ are generally preferred. However, in order to obtain, for example, chiral dopants for cholesteric or for chiral tilted smectic liquid crystals, preferably also one or both residues $R^3$ and $R^4$ can be branched-chain chiral and/or can have a group —CHX— in which X is halogen (preferably fluorine or chlorine), cyano or methyl in place of one methylene group. In order to obtain a high spontaneous polarization for chiral tilted smectic applications, the centre of chirality (that is, the chain branching or the halogen or cyano substituent) should preferably be close to the ring system, for example in the 1- or 2-position of the residue $R^3$ or $R^4$. Further, the tendency to form liquid crystalline phases basically remains when 1 methylene group or 2 non-adjacent methylene groups is/are replaced by —O—, —COO— and/or —OOC—, which can be employed, inter alia, for the preparation of chiral residues from natural, optically active acids, alcohols etc. (for example, 2-alkoxycarbonylethoxy from lactic acid).

Further, the mesophase range, the threshold potential, the response speed, the steepness of the transmission curve etc. can be varied by the selection of the position of the C=C double bond in unsaturated residues such as alkenyl, alkenyloxy and the like. The effect is fundamentally known for example, from Mol. Cryst. Liq. Cryst. 122, 241 (1985), 131, 109 (1985) and 148, 123 (1987). There are preferred residues which have the double bond in the 1-position (especially the E-isomer), in the 3-position (especially the E-isomer) or in the 4-position (especially the Z-isomer) of the chain including any hereto atoms, such as 1E-alkenyl, 3E-alkenyl, 4Z-alkenyl, 2E-alkenyloxy, 3Z-alkenyloxy and the like. Further, the double bond can also preferably be in the terminal position, especially in the case of compounds for smectic applications. Examples of preferred residues with the double bond in the terminal position are 6-heptenyl, 7-octenyl, 8-nonenyl, 9-decenyl, 10-undecenyl, 11-dodecenyl, 5-hexenyloxy, 6-heptenyloxy, 7-octenyloxy, 8-nonenyloxy, 9-decenyloxy, 10-undecenyloxy, 11-dodecenyloxy and the like.

The preparation of the compounds of formula I can be effected in a manner known per se. Preferred methods are illustrated on the basis of the following Schemes 1-4 in which $R^1$, $R^2$, $Z^1$, n and rings $A^1$ and $A^2$ have the above significances, L represents a leaving group (for example, rosylate), R denotes $C_1$-$C_{18}$-alkyl and $R^5$ is an alkyl group in which optionally one >CH—CH< is replaced by >C=C< and/or optionally a methylene group which is not present in the 1-position is replaced by —O—, —COO— or —OOC— and/or optionally one methylene group is replaced by —CHX— (wherein X has the above significance).

Scheme 1

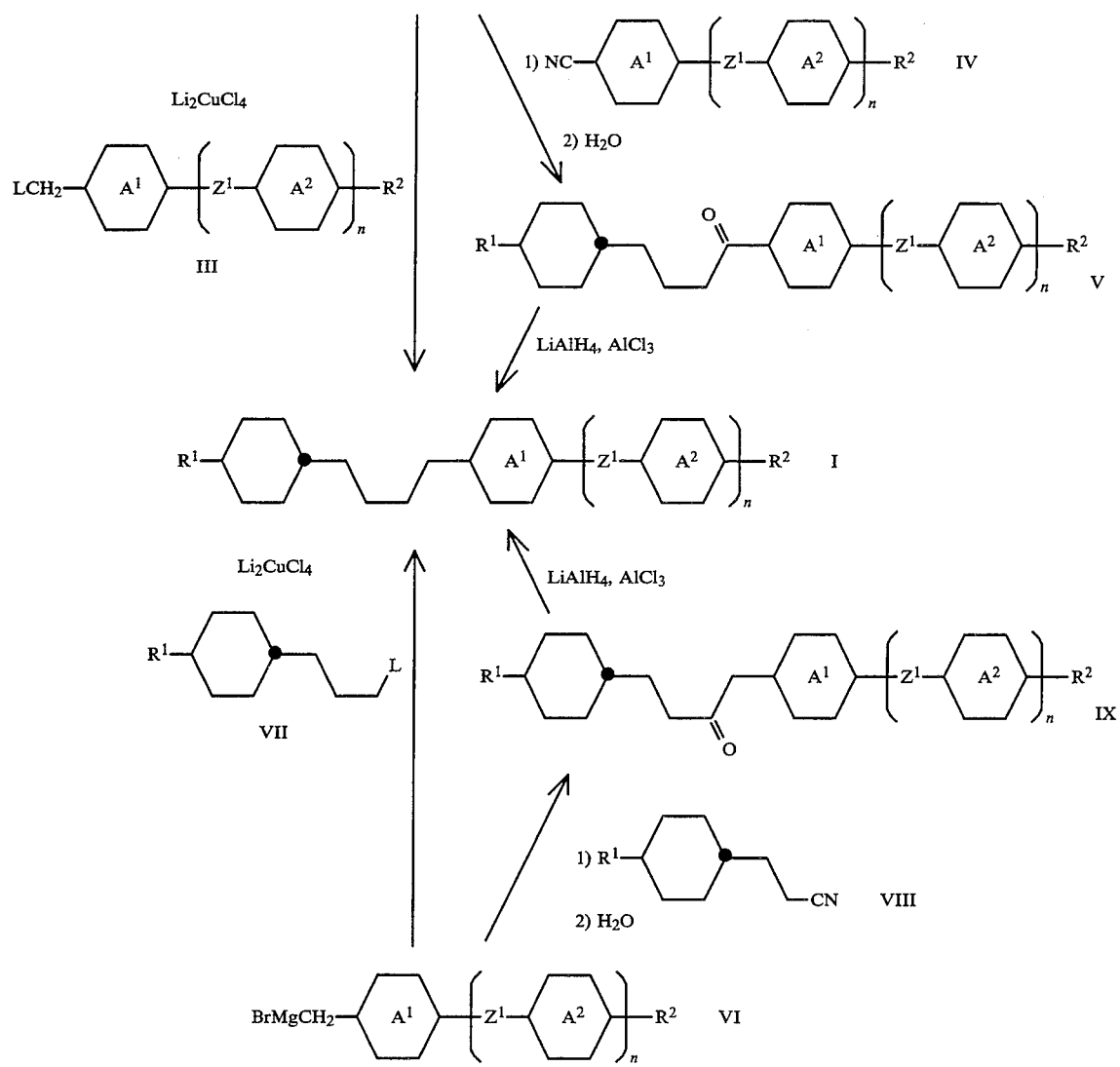
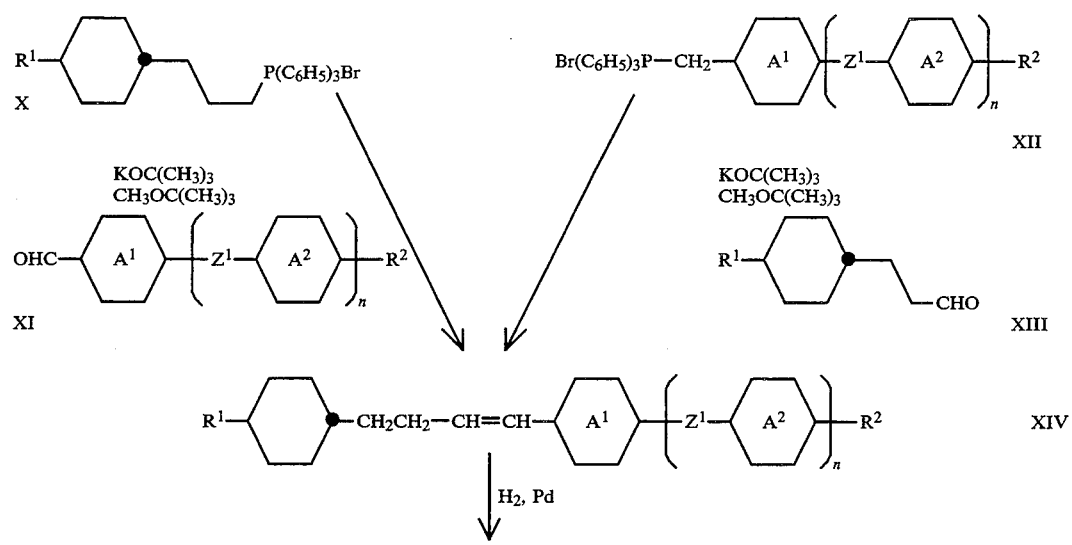

-continued
Scheme 2
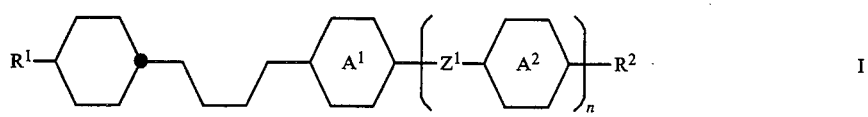
I
Scheme 3
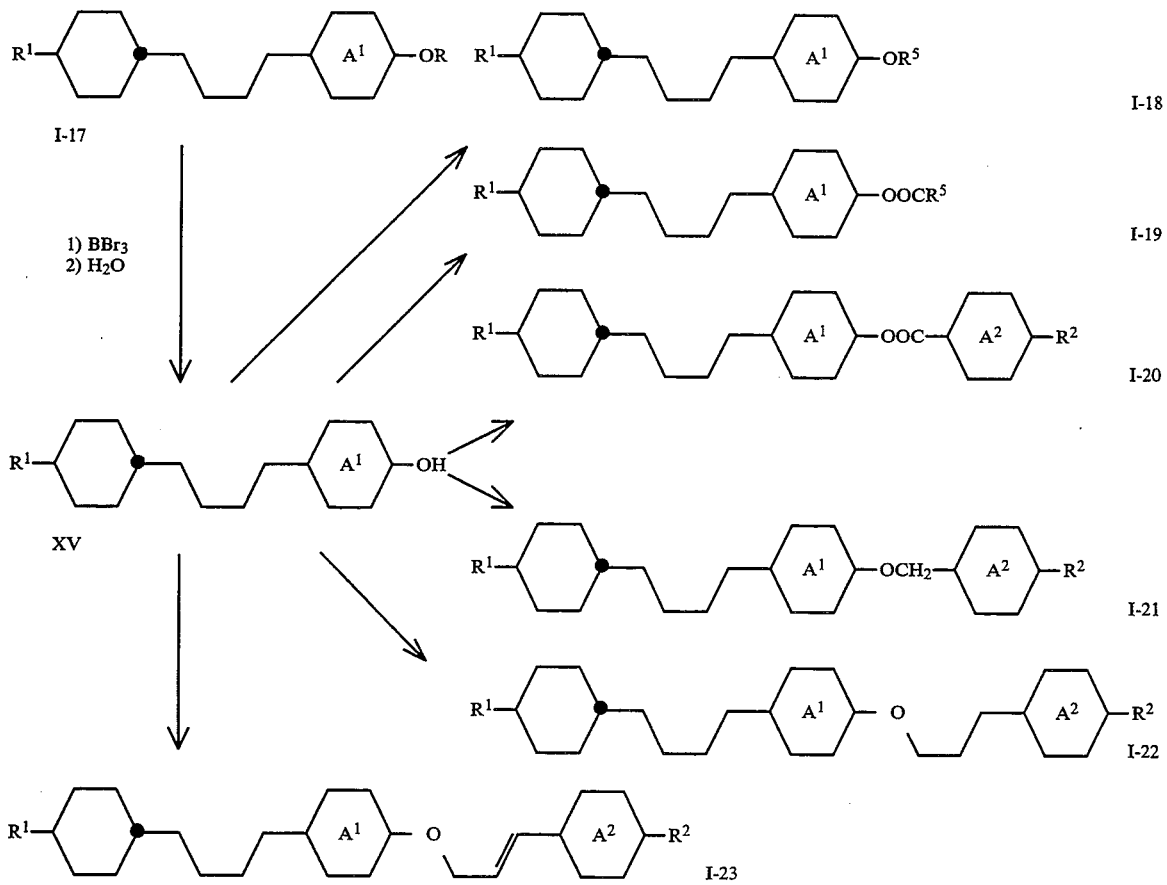
Scheme 4
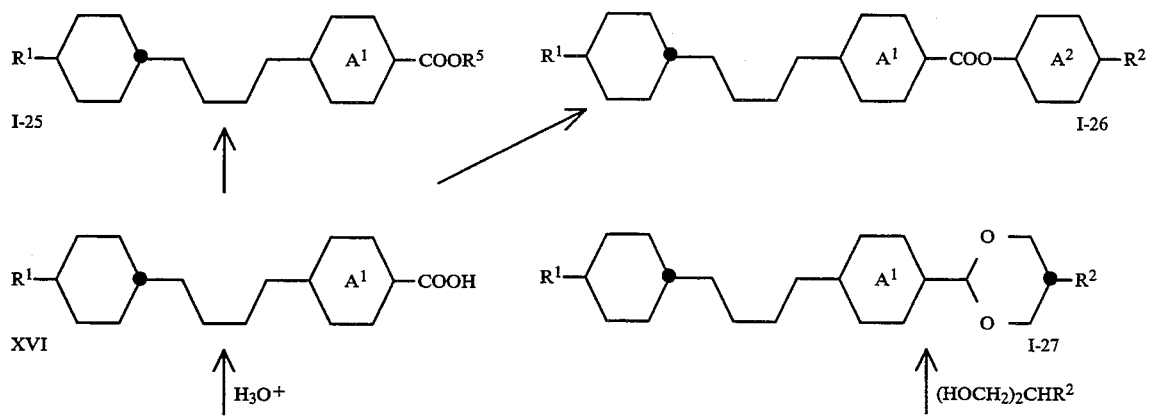

Scheme 4

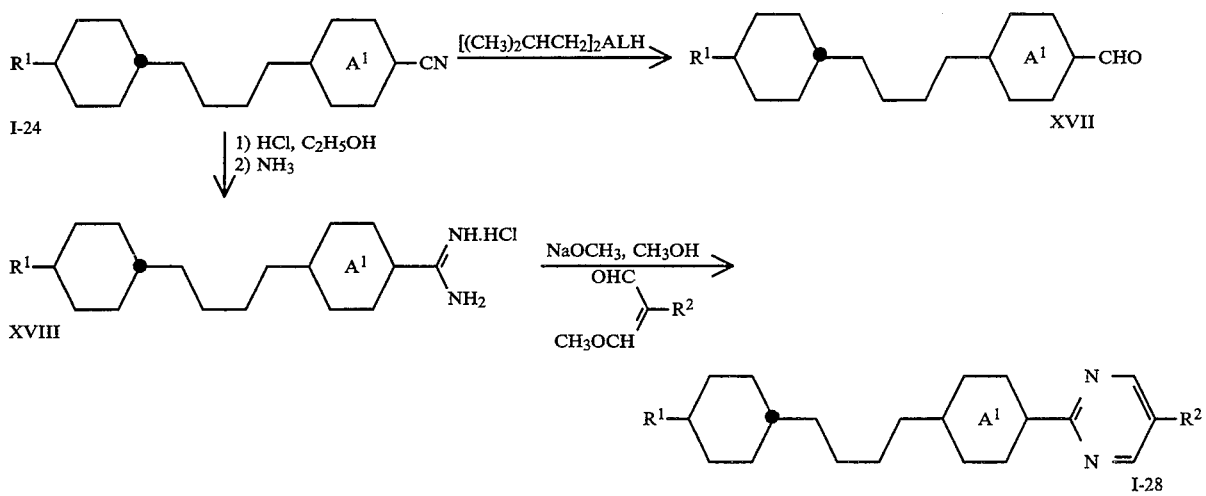

The starting materials are known or are analogues of known compounds and can be prepared according to known methods. In particular, the preparation of the Grignard reagents of Scheme 1 and of the phosphonium salts of Scheme 2 from the corresponding bromides is familiar to person skilled in the art. The nitriles of formulas IV and VIII and the aldehydes of formulas XI and XIII are known liquid crystals, known intermediates for liquid crystals or analogues of such compounds.

The linkage at other positions of the butane bridging group can be effected analogously to the reactions presented in Schemes 1 and 2.

In the case of the reduction with lithium aluminium hydride and aluminium chloride according to Scheme 1, there exists the risk of dioxane rings and ester groups being hydrogenated. Further, in the case of the catalytic hydrogenation according to Scheme 2 double bonds which can be present in the side-chains or in additional bridging groups ($Z^1$, $Z^2$ or $Z^3$) are also hydrogenated. Compounds of formula I having a dioxane ring or an ester function can, however, be obtained by a Fouquet-Schlosser reaction (for example, by reacting a compound of formula II with a compound of formula III or by reacting a compound of formula VI with a compound of formula VII) or according to Scheme 2. On the other hand, compounds with double bends can be reacted according to the methods illustrated in Scheme 1.

Preferably, however, ether and ester functions, heterocyclic rings, C=C double bonds etc. are formed only after the synthesis of the butane bridging group. Suitable methods will be familiar to a person skilled in the art from the preparation of known liquid crystal materials. Examples of such reactions are illustrated in Schemes 3 and 4. Further methods as well as the introduction of alkenyl substituents and chain-lengthening reactions are disclosed for example, in EP—A-0122389, EP—A-0169327, EP—A-0172360, EP—A-0167912, EP—A-0168683 and EP—A-0242716.

The etherification of a compound of formula XV to give a compound of formula I-18, I-21, I-22 or I-23 can be effected in a manner known per se, for example, by reaction with the corresponding bromide or iodide in the presence of potassium carbonate. Compounds of formula I-18 which have an ester group in $R^5$ can preferably also be prepared by reacting a compound of formula XV with the corresponding hydroxyester in the presence of triphenylphosphine and diethyl azodicarboxylate.

The preparation of the esters of formulas I-19, I-20, I-25 and I-26 can be effected according to esterification methods which are known per se, for example by reacting compound of formula XV with the corresponding carboxylic acid or by reacting a compound of formula XVI with the corresponding alcohol or phenol in the presence of 4-(dimethylamino)pyridine and N,N'-dicyclohexylcarbodiimide.

The compounds of formula I can be used in the form of mixtures with one another and/or with other liquid crystal components. Suitable liquid crystal components are known to a person skilled in the art in large numbers, for example, from D. Demus et al., Flussige Kristalle in Tabellen, VEB Deutscher Verlag fur Grundstoffindustrie, Leipzig, volumes I and II, and many of them are, moreover, commercially available.

The invention is accordingly also concerned with a liquid crystalline mixture having at least 2 components, wherein at least one component is a compound of formula (especially one of the compounds referred to as being preferred).

Having regard to the good solubility and on the other hand to the large breadth of variation of the properties and fields of application, the amount of compounds of formula I in the mixtures in accordance with the invention can vary in a wide range and can amount to about 0.1 to 100 wt. %. For example, the mixture can consist of compounds of formula I. On the other hand, for example, chiral dopants are frequently used only in relatively small amounts, for example, about 0.1 to 10 wt. %. In general, however, the amount of compounds of formula I in the mixtures in accordance with the invention amounts to about 1–60wt. %. A range of about 5–30 wt. % is generally preferred.

The mixtures in accordance with the invention for nematic or cholesteric applications preferably contain, in addition to one or more compounds of formula I, one or more compounds from the group of compounds of the formula

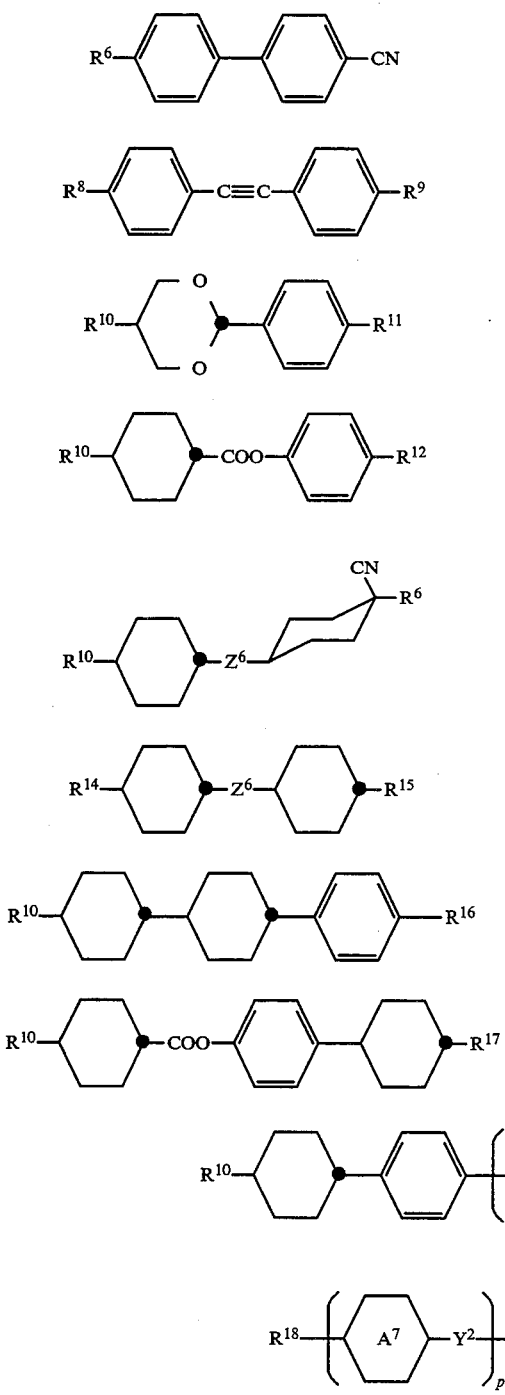

wherein $R^6$ is alkyl, 3E-alkenyl or 4-alkenyl; $R^7$ represents cyano or fluorine; $R^8$ and $R^9$ denote alkyl or alkoxy; $R^{10}$ and $R^{17}$ each independently are alkyl, 1E-alkenyl, 3E-alkenyl or 4-alkenyl; $R^{11}$ denotes cyano, —NCS, alkyl, 1E-alkenyl, 3E-alkenyl, 4-alkenyl, alkoxy, 2E-alkenyloxy or 3-alkenyloxy; $R^{12}$ is alkoxy, 2E-alkenyloxy or 3-alkenyloxy; p stands for the number 0 or 1; $Z^6$ represents a single covalent bond or —CH$_2$CH$_2$—; $R^{13}$ is cyano, alkyl, 1E-alkenyl, 3E-alkenyl or 4-alkenyl; $R^{14}$ denotes alkyl, 1E-alkenyl or 4-alkenyl; $R^{15}$ represents alkoxy, 2E-alkenyloxy or 3-alkenyloxy; $R^{16}$ denotes cyano, alkyl, 1E-alkenyl, 3E-alkenyl, 4-alkenyl, alkoxy, 2E-alkenyloxy or 3-alkenyloxy; $X^5$ denotes fluorine or chlorine and $X^6$ denotes hydrogen, fluorine or chlorine; $R^{18}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and rings and $A^7$ and $A^8$ each independently represent trans-1,4-cyclohexylene in which optionally 2 non-adjacent CH$_2$ groups are replaced by oxygen or 1,4-phenylene in which optionally 1 CH group or 2 CH groups is/are replaced by nitrogen.

Preferably, each of the residues $R^6$ and $R^8$–$R^{18}$ has a maximum of 12 carbon atoms, especially a maximum of 7 carbon atoms.

The mixtures in accordance with the invention for smectic applications (especially for tilted smectic or chiral tilted smectic phases) preferably contain, in addition to one or more compounds of formula I, one or more compounds from the group of compounds of formula

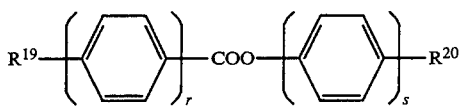
XXXVII

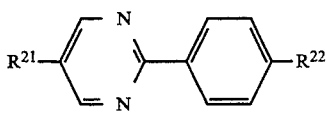
XXXVIII

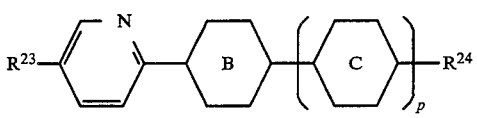
XXXIX

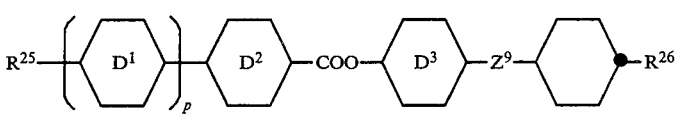
XL

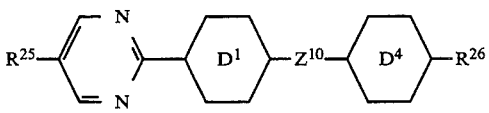
XXXXI

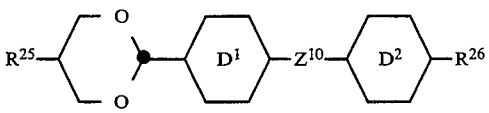
XXXXII

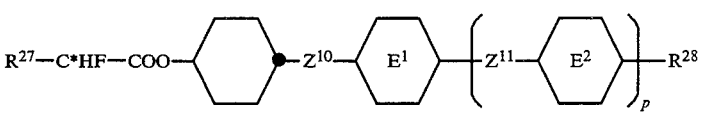
XXXXIII

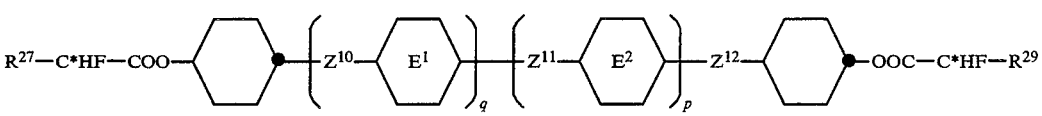
XXXXIV wherein $R^{19}$ and $R^{20}$ denote alkyl, alkoxy, alkenyloxy, alkanoyloxy or alkoxycarbonyl with up to 18 carbon atoms; r and s each independently are 1 or 2; $R^{21}$ and $R^{22}$ denote alkyl, alkoxy or alkenyloxy with up to 18 carbon atoms; ring B represents unsubstituted or halogen- and/or methyl-substituted 1,4-phenylene; ring C represents trans-1,4-cyclohexylene or unsubstituted or halogen- and/or methyl-substituted 1,4-phenylene; p and q each independently stand for the number 0 or 1; $R^{23}$ and $R^{24}$ each independently denote an unsubstituted or halogen-substituted $C_1$–$C_{18}$-alkyl or $C_2$–$C_{18}$-alkenyl group in which optionally one $CH_2$ group or two non-adjacent $CH_2$ groups is/are replaced by —O—, —COO— and/or —OOC—; rings $D^1$ $D^2$ and $D^3$ each independently represent unsubstituted or cyano-, halogen- or lower alkyl-substituted 1,4-phenylene; $Z^9$ denotes a single covalent bond, —$CH_2CH_2$—, —$OCH_2$—, —COO— or —OOC—; $R^{25}$ and $R^{26}$ each independently are an unsubstituted or halogen-substituted $C_1$–$C_{18}$-alkyl or $C_2$–$C_{18}$-alkenyl group in which optionally one $CH_2$ group or two non-adjacent $CH_2$ groups is/are replaced by oxygen; ring $D^4$ represents trans-1,4-cyclohexylene or unsubstituted or cyano-, halogen- or lower alkyl-substituted 1,4-phenylene; $Z^{10}$, $Z^{11}$ and $Z^{12}$ each independently denote a single covalent bond, —COO—, —OOC—, —$CH_2CH_2$—, —$OCH_2$— or —$CH_2O$—; $R^{27}$ and $R^{29}$ each independently are a $C_1$–$C_{15}$-alkyl or $C_2$–$C_{15}$-alkenyl group in which optionally one $CH_2$ group is replaced by oxygen; $R^{28}$ denotes an unsubstituted or halogen-substituted $C_1$–$C_{15}$-alkyl or $C_2$–$C_{15}$-alkenyl group in which optionally one $CH_2$ group is replaced by oxygen and/or optionally one $CH_2$ group is replaced by an ester group —COO— or —OOC—; rings $E^1$ and $E^2$ each independently represent unsubstituted or halogen-, cyano- and/or methyl-substituted 1,4-phenylene in which optionally 1 CH group or 2 CH groups is/are replaced by nitrogen; and C* denotes a chiral carbon atom.

The preparation of the liquid crystalline mixtures and of the electro-optical devices can be effected in a manner known per se.

The invention is illustrated in more detail by the following Examples. The optical antipodes of chiral compounds have in each case the same transition temperatures and the same absolute values of the twisting, but with opposite signs. The abbreviations used for the characterization of the phase transitions have the following significances:

C stands for crystalline
S stands for smectic
$S_A$, $S_B$, $S_C$ etc. stand for smectic A, B, C etc.
$S_C^*$, $S_F^*$ etc. stand for chiral smectic C, F etc.
N stands for nematic
N* stands for cholesteric
I stands for isotropic.

EXAMPLE 1

A mixture of 19 g of 1-butyloxy-4-[4-(trans-4-pentylcyclohexyl)-1-butenyl]benzene (cis/trans mixture), 200 ml of absolute toluene and 100 ml of absolute ethyl acetate: was treated with 2 g of palladium/carbon (10%) and hydrogenated at normal pressure and room temperature until the hydrogen uptake came to a standstill. The inorganic material was removed by filtration and the filtrate was concentrated. The residue was purified by chromatography on silica gel with toluene/ethyl acetate. Recrystallization from ethanol gave 16 g of pure 1-butyloxy-4-[4-(trans-4-pentylcyclohexyl)-1-butyl]benzene with m.p. (C-$S_B$) 29° C. and cl.p. ($S_B$—I) 43° C.

The 1-butyloxy-4-[4-(trans-4-pentylcyclohexyl)-1-butenyl]benzene used as the starting material was prepared as follows:

A mixture of 54 g of (4-butyloxyphenyl)methyl-triphenylphosphonium bromide and 450 ml of absolute t-butyl methyl ether was treated with 12 g of solid potassium t-butylate at 0° C. and while gassing with nitrogen. After completion of the addition the reaction mixture was stirred at 0° C. for a further 15 minutes (whereby a deep orange coloration resulted) and then treated within 30 minutes at 0° C. with a solution of 15 g of 3-(trans-4-pentylcyclohexyl)propionaldehyde in 150 ml of absolute t-butyl methyl ether. Subsequently, the reaction mixture was stirred at room temperature overnight and then poured into 1000 ml of water and extracted three times with 200 ml of diethyl ether each time. The organic phases were washed twice with 500 ml of concentrated sodium chloride solution each time, dried over magnesium sulfate, filtered and subsequently concentrated. Chromatography of the residue on silica gel with hexane/toluene (vol. 4:1) gave 21 g of 1-butyloxy-4-[4-(trans-4-pentylcyclohexyl)-1-butenyl]-benzene (cis/trans mixture). Recrystallization from ethanol gave pure trans isomer with m.p. (C-$S_B$) 46° C., $S_B$—$S_A$ 74° C., $S_A$—N 76° C. and cl.p. (N—I) 91° C.

The following compounds can be prepared in an analogous manner:

1-Fluoro-4-[4-(trans-4-pentylcyclohexyl)-1-butyl]-benzene, m.p. (C-I) 13° C., cl.p. (N-I) −17° C.;
1-chloro-4-[4-(trans-4-pentylcyclohexyl)-1-butyl]benzene;
1-bromo-4-[4-(trans-4-pentylcyclohexyl)-1-butyl]benzene;
1-iodo-4-[4-(trans-4-pentylcyclohexyl)-1-butyl]benzene;
1,2-difluoro-4-[4-(trans-4-pentylcyclohexyl)-1-butyl]-benzene, m.p. (C-I) 6° C.;
1-methyl -4-[4-(trans-4-pentylcyclohexyl)-1-butyl]benzene;
1-(trifluoromethyl)-4-[4-(trans-4-pentylcyclohexyl)-1-butyl]benzene;
1-(trifluoromethoxy)-4-[4-(trans-4-pentylcyclohexyl)-1-butyl]benzene, m.p. (C-I) 18° C., cl.p. (N-I) −12° C.;
4-[4-(trans-4-pentylcyclohexyl)-1-butyl]benzonitrile, m.p. (C-I) 51° C., cl.p. (N-I) 39° C.;
1-fluoro-4- [4-(trans-4-[trans-4-propylcyclohexyl]cyclohexyl)-1-butyl]benzene, m.p. (C-S) 56° C., S-N 87° C., cl.p. (N-I) 116° C.;
1,2-difluoro-4-[4-(trans-4-[trans-4-propylcyclohexyl]cyclohexyl)-1-butyl]benzene, m.p. (C-S) 39° C., S-N 69° C., cl.p. (N-I) 103° C.;
1-methyl-4-[4-(trans-4-[trans-4-propylcyclohexyl]cyclohexyl)-1-butyl]benzene;
1-(trifluoromethyl)-4-[4-(trans-4-[trans-4-propylcyclohexyl]cyclohexyl)-1-butyl]benzene;
1-(trifluoromethoxy)-4-[4-(trans-4-[trans-4-propylcyclohexyl]cyclohexyl)-1-butyl]benzene, m.p. (C-S) 47° C., S-N 86° C., cl.p. (N-I) 111° C.;
4-[4-(trans-4-[trans-4-propylcyclohexyl]cyclohexyl)-1-butyl]benzonitrile;
2-fluoro-4-[4-(trans-4-[trans-4-propylcyclohexyl]cyclohexyl)-1-butyl]benzonitrile;
1-ethoxy-2,3-difluoro-4-[4-(trans-4-[trans-4-propylcyclohexyl]cyclohexyl)-1-butyl]benzene;
1-fluoro-4-[4-(trans-4-[trans-4-pentylcyclohexyl]cyclohexyl)-1-butyl]benzene;
1,2-difluoro-4-[4-(trans-4-[trans-4-pentylcyclohexyl]cyclohexyl)-1-butyl]benzene;
1-methyl-4-[4-(trans-4-[trans-4-pentylcyclohexyl]cyclohexyl)-1-butyl]benzene;
1-(trifluoromethyl)-4-[4-(trans-4-[trans-4-pentylcyclohexyl]cyclohexyl)-1-butyl]benzene;
1-(trifluoromethoxy)-4-[4-(trans-4-[trans-4-pentylcyclohexyl]cyclohexyl)-1-butyl]benzene;
4-[4-(trans-4-[trans-4-pentylcyclohexyl]cyclohexyl)-1-butyl]benzonitrile;
2-fluoro-4-[4-(trans-4-[trans-4-pentylcyclohexyl]cyclohexyl)-1-butyl]benzonitrile;
1-ethoxy-2,3-difluoro-4-[4-(trans-4-[trans-4-pentylcyclohexyl]cyclohexyl)-1-butyl]benzene.

EXAMPLE 2

A mixture of 0.3 g of 4-[4-(trans-4-pentylcyclohexyl)-1-butyl]phenol, 0.14 g of methyl iodide, 0.6 g of potassium carbonate and 50 ml of absolute butanone was heated to reflux overnight. Subsequently, the cooled reaction mixture was poured into water and extracted three times with 50 ml of diethyl ether each time. The combined organic phases were washed with 500 ml of water, dried over magnesium sulfate, filtered and concentrated. Chromatography of the residue on silica gel with toluene and recrystallization from ethanol gave pure 1-methoxy-4-[4-(trans-4-pentylcyclohexyl)-1-butyl]benzene with m.p. (C-I) 27° C. and cl.p. ($S_B$-I) 16° C.

The 4-[4-(trans-4-pentylcyclohexyl)-1-butyl]phenol used as the starting material was prepared as follows:

A mixture of 16 g of 1-butyloxy-4-[4-(trans-4-pentylcyclohexyl)-1-butyl]benzene and 100 ml of absolute dichloromethane was treated at 0° C. and while gassing with nitrogen with 50 ml of a 1M solution of boron tribromide in dichloromethane. After completion of the addition the reaction mixture was stirred at room temperature for a further 2 hours and then treated cautiously with 200 ml of water. The organic phase was separated and the aqueous phase was back-extracted three times with 100 ml of dichloromethane each time.

The combined organic phases were washed in succession with 1000 ml of water, 500 ml of dilute potassium carbonate solution and again with 1000 ml of water, dried over magnesium sulfate, filtered and subsequently concentrated. Recrystallization of the residue from hexane gave 11 g of pure 4-[4-(trans-4-pentylcyclohexyl)-1-butyl]phenol with m.p. 86° C.

The following compounds can be prepared in an analogous manner:

1-Ethoxy-4-[4-(trans-4-pentylcyclohexyl)-1-butyl]benzene, m.p. (C-$S_B$) 18° C., cl.p. ($S_B$-I) 31° C.;

1-propyloxy-4-[4-(trans-4-pentylcyclohexyl)-1-butyl]benzene, m.p. (C-I) 39° C., cl.p. ($S_B$-I) 28° C.;

1-pentyloxy-4-[4-(trans-4-pentylcyclohexyl)-1-butyl]benzene; m.p. (C-$S_B$) 31° C., cl.p. ($S_B$-I) 39° C.;

1-hexyloxy-4-[4-(trans-4-pentylcyclohexyl)-1-butyl]benzene;

1-heptyloxy-4-[4-(trans-4-pentylcyclohexyl)-1-butyl]benzene;

1-octyloxy-4-[4-(trans-4-pentylcyclohexyl)-1-butyl]benzene;

1-[(trans-4-pentylcyclohexyl)methoxy]-4-[4-(trans-4-pentylcyclohexyl)-1-butyl]benzene, m.p. (C-$S_B$) 42° C., cl.p. ($S_B$-I) 108° C.;

1-[3-(trans-4-pentylcyclohexyl)-1-propyloxy]-4-[4-(trans-4-pentylcyclohexyl)-1-butyl]benzene, m.p. (C-$S_B$) 52° C., cl.p. ($S_B$-I) 94° C.;

1-[3E-(trans-4-pentylcyclohexyl)allyloxy]-4-[4-(trans-4-pentylcyclohexyl)-1-butyl]benzene, m.p. (C-S) 77° C., S-$S_B$ 94° C., $S_B$-N 99° C., cl.p. (N-I) 107° C.

EXAMPLE 3

1.9 g of 2,3-difluoro-4-heptyloxybenzoic acid, 2 g of 4-[4-(trans-4-pentylcyclohexyl)-1-butyl]phenol and 0.1 g of 4-(dimethylamino)pyridine were dissolved in 250 ml of dichloromethane and the solution was treated portionwise within 10 minutes while stirring with 1.6 g of N,N'-dicyclohexylcarbodiimide. The mixture was stirred at room temperature overnight and then filtered. The filtrate was diluted with dichloromethane, washed twice with 50 ml of saturated sodium carbonate solution each time and then with water, dried over magnesium sulfate, filtered and then concentrated. Chromatography of the residue on silica gel with toluene/ethyl acetate (vol. 4:1) and recrystallization from ethanol gave 2 g of 2,3-difluoro-4-heptyloxybenzoic acid 4-[4-(trans-4-pentylcyclohexyl)-1-butyl]phenyl ester with m.p. (C-$S_C$) 67° C., $S_C$-N 70° C. and cl.p. (N-I) 128° C.

The following compounds can be prepared in an analogous manner:

2,3-Difluoro-4-octyloxybenzoic acid 4-[4-(trans-4-pentylcyclohexyl)-1-butyl]phenyl ester, m.p. (C-$S_C$) 70° C., $S_C$-N 82° C., cl.p. (N-I) 123° C.;

2,3-difluoro-4-nonyloxybenzoic acid 4-[4-(trans-4-pentylcyclohexyl)-1-butyl]phenyl ester, m.p. (C-$S_C$) 71° C., $S_C$-N 91° C., cl.p. (N-I) 121° C.;

2,3-difluoro-4-decyloxybenzoic acid 4-[4-(trans-4-pentylcyclohexyl)-1-butyl]phenyl ester, m.p. (C-$S_C$) 69° C., $S_C$-N 96° C., cl.p. (N-I) 120° C.;

2,3-difluoro-4-undecyloxybenzoic acid 4-[4-(trans-4-pentylcyclohexyl)-1-butyl]phenyl ester, m.p. (C-$S_C$) 58° C., $S_C$-N 103° C., cl.p. (N-I) 119° C.;

2,3-difluoro-4-dodecyloxybenzoic acid 4-[4-(trans-4-pentylcyclohexyl)-1-butyl]phenyl ester, m.p. (C-$S_C$) 56° C., $S_C$-N 107° C., cl.p. (N-I) 118° C.;

trans-4-pentylcyclohexanecarboxylic acid 4-[4-(trans-4-pentylcyclohexyl)-1-butyl]phenyl ester, m.p. (C-$S_B$) 59° C., $S_B$-N 135° C., cl.p. (N-I) 139° C.;

4-[4-(trans-4-pentylcyclohexyl)-1-butyl]-4'-[2(R)-fluorohexanoyloxy]biphenyl, m.p. (C-$S_B$) 68° C., cl.p. ($S_B$-I) 140° C.

EXAMPLE 4

2 g of 4-[4-(trans-4-pentylcyclohexyl)-1-butyl]benzoic acid, 0.7 g of 4-fluorophenol, 1.5 g of N,N'-dicyclohexylcarbodiimide, 0.1 g of 4-(dimethylamino)pyridine and 100 ml of dichloromethane were reacted in an analogous manner to Example 3. This gave 1.8 g of 4-[4-(trans-4-pentylcyclohexyl)-1-butyl]benzoic acid 4-fluorophenyl ester with m.p. (C-N) 63° C. and cl.p. (N-I) 104° C.

The 4-[4-(trans-4-pentylcyclohexyl)-1-butyl]benzoic acid used as the starting material was prepared as follows:

A mixture of 36 g of 4-[4-(trans-4-pentylcyclohexyl)-1-butyl]benzonitrile, 300 ml of concentrated sulfuric acid, 300 ml of glacial acetic acid and 300 ml of water was heated to 120° C. overnight. The cooled reaction mixture was poured into 2000 ml of water and the resulting precipitate was removed by filtration under suction, sucked dry, washed with a large amount of water and subsequently recrystallized from ethanol. This gave 28 g of pure 4-[4-(trans-4-pentylcyclohexyl)-1-butyl]benzoic acid with m.p. (C-N) 195° C. and cl.p. (N-I) 199° C.

The following compounds can be prepared in an analogous manner:

4-[4-(trans-4-Pentylcyclohexyl)-1-butyl]benzoic acid 4-chlorophenyl ester, m.p. (C-N) 75° C., cl.p. (N-I) 126° C.;

4-[4-(trans-4-pentylcyclohexyl)-1-butyl]benzoic acid 4-bromophenyl ester, m.p. (C-N) 80° C., $S_A$-N 58° C., cl.p. (N-I) 128° C.;

4-[4-(trans-4-pentylcyclohexyl)-1-butyl]benzoic acid 4-iodophenyl ester, m.p. (C-N) 92° C., cl.p. (N-I) 125° C.;

4-[4-(trans-4-pentylcyclohexyl)-1-butyl]benzoic acid 4-cyanophenyl ester, m.p. (C-N) 78° C., cl.p. (N-I) 151° C.;

4-[4-(trans-4-pentylcyclohexyl)-1-butyl]benzoic acid 2-fluoro-4-cyanophenyl ester;

4-[4-(trans-4-pentylcyclohexyl)-1-butyl]benzoic acid 3-fluoro-4-cyanophenyl ester, m.p. (C-N) 59° C., cl.p. (N-I) 132° C.;

4-[4-(trans-4-pentylcyclohexyl)-1-butyl]benzoic acid 3,4-difluorophenyl ester, m.p. (C-N) 50° C., cl.p. (N-I) 88° C.; 4-[4-(trans-4-pentylcyclohexyl)-1-butyl]benzoic acid 2,3-difluoro-4-ethoxyphenyl ester;

4-[4-(trans-4-pentylcyclohexyl)-1-butyl]benzoic acid 2,3-dicyano-4-pentylphenyl ester; 4-[4-(trans-4-pentylcyclohexyl)-1-butyl]benzoic acid 4-methylphenyl ester;

4-[4-(trans-4-pentylcyclohexyl)-1-butyl]benzoic acid 4-propylphenyl ester;

4-[4-(trans-4-pentylcyclohexyl)-1-butyl]benzoic acid 4-pentylphenyl ester;

4-[4-(trans-4-pentylcyclohexyl)-1-butyl]benzoic acid trans-4-propylcyclohexyl ester;

4-[4-(trans-4-pentylcyclohexyl)-1-butyl]benzoic acid 4-trifluoromethoxyphenyl ester, m.p. (C-N) 71° C., cl.p. (N-Z) 109 ° C.

EXAMPLE 5

A solution of 3 g of 4-[4-(trans-4-pentylcyclohexyl)-1-butyl]benzaldehyde and 1.7 g of 2-pentyl-1,3-propanediol in 50 ml of toluene was treated with 2 drops of 10% (vol.) sulfuric acid. The mixture was heated to boiling for 2 hours, whereby the resulting water was distilled off simultaneously. Then, 4 drops of triethylamine were added to the reaction mixture. After cooling the mixture was washed with 50 ml of 1N sodium hydrogen carbonate solution and twice with 50 ml of water each time, dried over magnesium sulfate, filtered and subsequently concentrated. Chromatography of the residue on silica gel with toluene and recrystallization from acetone gave 1.2 g of trans-5-pentyl-2-(4-[4-(trans-4-pentylcyclohexyl)-1-butyl]phenyl-1,3-dioxane with m.p. (C-N) 73° C. and clop. (N-Z) 106° C.

The 4-[4-(trans-4-pentylcyclohexyl)-1-butyl]benzaldehyde used as the starting material was prepared as follows:

A solution of 10 g of 4-[4-(trans-4-pentylcyclohexyl)-1-butyl]benzonitrile in 200 ml of absolute dichloromethane was treated at −78° C. and while gassing with nitrogen with 50 ml of a solution of diisobutylaluminium hydride in hexane (vol. 20%). After completion of the addition the reaction mixture was stirred at room temperature for a further 8 hours and then treated with 200 ml of water and extracted three times with 100 ml of dichloromethane each time. The combined organic phases were washed twice with 500 ml of water each time, dried over magnesium sulfate, filtered and concentrated. This gave 7.5 g of 4-[4-(trans-4-pentylcyclohexyl)-1-butyl]benzaldehyde.

The following compounds can be prepared in an analogous manner:

trans-5-Propyl-2-(4-[4-(trans-4-propylcyclohexyl)-1-butyl]phenyl)-1,3-dioxane;

trans-5-propyl-2-(4-[4-(trans-4-pentylcyclohexyl)-1-butyl]phenyl)-1,3-dioxane;

trans-5-Pentyl-2-(4-[4-(trans-4-propylcyclohexyl)-1-butyl]phenyl)-1,3-dioxane.

EXAMPLE 6

A mixture of 1.3 g of lithium aluminium hydride and 100 ml of absolute diethyl ether was placed at 0° C. and while gassing with nitrogen and treated with a solution 10 g of aluminium chloride and 200 ml of absolute diethyl ether. After completion of the addition the mixture was stirred at room temperature for a further 20 minutes and treated within 30 minutes with a solution of 9 g of 1-(trans-4-pentylcyclohexyl)-4-[4-(trans-4-pentylcyclohexyl)butanoyl]benzene and 100 ml of absolute dichloromethane. After completion of the addition the reaction mixture was heated overnight under slight reflux, then cooled to 0° C. and treated with 50 ml of water and 500 ml of 25% hydrochloric acid. The organic phase was separated and the aqueous phase was back-extracted three times witch 100 ml of diethyl ether each time. The combined organic phases were washed with 500 ml of water, 250 ml of concentrated potassium carbonate solution and again with 500 ml of water, dried over magnesium sulfate, filtered and subsequently concentrated. Chromatography of the residue on silica gel with toluene and recrystallization from acetone gave 5.7 g of 1-(trans-4-pentylcyclohexyl)-4-[4-(trans-4-pentylcyclohexyl)-1-butyl]benzene with m.p. (C-$S_B$) 50° C. and cl.p. ($S_B$-I) 111° C.

The 1-(trans-4-pentylcyclohexyl)-4-[4-(trans-4-pentylcyclohexyl)butanoyl]benzene used as the starting material was prepared as follows:

0.6 g of magnesium shavings was covered with 5 ml of absolute diethyl ether while gassing with nitrogen and then, after the addition of a crystal of iodine, treated with a solution of 7 g of 3-(trans-4-pentylcyclohexyl)-1-propyl bromide in 50 ml of absolute diethyl ether. After completion of the addition the mixture was heated to reflux for a further 30 minutes. The reaction mixture was then treated with a solution of 2.6 g of 4-(trans-4-pentylcyclohexyl)benzonitrile in 50 ml of absolute diethyl ether and subsequently heated overnight under slight reflux. The cooled reaction mixture was treated with 200 ml of 25% hydrochloric acid and the organic phase was separated. The aqueous phase was extracted three times with 50 ml of diethyl ether each time. The combined organic phases were washed with 500 ml of water, 250 ml of concentrated potassium carbonate solution and again with 500 ml of water, dried over magnesium sulfate, filtered and then concentrated. Recrystallization of the residue from ethanol gave 4.1 g of 1-(trans-4-pentylcyclohexyl)-4-[4-(trans-4-pentylcyclohexyl)butanoyl]benzene with m.p. (C-$S_B$) 75° C., $S_B$-N 89° C. and cl.p. (N-I) 116° C.

The following compounds can be prepared in an analogous manner:

1-(trans-4-Propylcyclohexyl)-4-[4-(trans-4-propylcyclohexyl)-1-butyl]benzene;

1-(trans-4-propylcyclohexyl)-4-[4-(trans-4-pentylcyclohexyl)-1-butyl]benzene;

1-(trans-4-pentylcyclohexyl)-4-[4-(trans-4-propylcyctohexyl)-1-butyl]benzene;

4-(trans-4-propylcyclohexyl)-4'-[4-(trans-4-propylcyclohexyl)-1-butyl]biphenyl;

4-(trans-4-propylcyclohexyl)-4'-[4-(trans-4-pentylcyclohexyl)-1-butyl]biphenyl; 4-[2(S)-methylbutyloxy]-4'-[4-(trans-4-pentylcyclohexyl)-1-butyl]biphenyl;

1-[2-(trans-4-pentylcyclohexyl)-1-ethyl]-4-[4-(trans-4-pentylcyclohexyl)-1-butyl]benzene;

2-(4-[4-(trans-4-pentylcyclohexyl)-1-butyl]phenyl-5-propylpyridine;

2-(4-[4-(trans-4-pentylcyclohexyl)-1-butyl]phenyl-5-butylpyridine;

2-(4-[4-(trans-4-pentylcyclohexyl)-1-butyl]phenyl-5-pentylpyridine;

2-(4-[4-(trans-4-pentylcyclohexyl)-1-butyl]phenyl-5-hexylpyridine;

2-(4-[4-(trans-4-pentylcyclohexyl)-1-butyl]phenyl-5-heptylpyridine;

2-(4-[4-(trans-4-pentylcyclohexyl)-1-butyl]phenyl-5-octylpyridine;

2-(4-[4-(trans-4-pentylcyclohexyl)-1-butyl]phenyl-5-nonylpyridine;

2-(4-[4-(trans-4-pentylcyclohexyl)-1-butyl]phenyl-5-decylpyridine;

1-(4-[4-(trans-4-pentylcyclohexyl)-1-butyl]phenyl-4-pentylbicyclo[2.2.2]octane;

($4\alpha H,8a\beta H$)-decahydro-$2\alpha$-(4-[4-(trans-4-pentylcyclohexyl)-1-butyl]phenyl)-$6\beta$-pentylnaphthalene.

EXAMPLE 7

A solution of 4 g of 4-hydroxy-4'-[4-(trans-4-pentylcyclohexyl)-1-butyl]biphenyl, 1.3 g of ethyl L(−)-lactate, 2.9 g of triphenylphosphine and 100 ml of tetrahydrofuran was treated with 1.9 g of diethyl azodicarboxylate. The reaction mixture was stirred at room temperature overnight, then concentrated and suspended with 100 ml of hot hexane. The precipitate which thereby resulted was removed by filtration and the filtrate was concentrated. Chromatography of the residue on silica gel with toluene/ethyl acetate (vol. 4:1) and recrystallization from ethanol gave 2.9 g of pure ethyl 2(R)-[4'-[4-(trans-4-pentylcyclohexyl)-1-butyl]-4- biphenylyloxy]propionate with m.p. (C-S$_B$) 71° C. and cl.p. (S$_B$-I) 76° C.

The 4-hydroxy-4'-[4-(trans-4-pentylcyclohexyl)-1-butyl]biphenyl used as the starting material was prepared as follows:

A solution of 2.5 g of (S)-4-(2-methylbutyl)oxy-4'-[4-(trans-4-pentylcyclohexyl)-1-butyl]biphenyl and 100 ml of absolute dichloromethane was reacted with 7 ml of a 1M solution of boron tribromide and dichloromethane in an analogous manner to Example 2. This gave 2.2 g of pure 4-hydroxy-4'-[4-(trans-4-pentylcyclohexyl)-1-butyl]biphenyl with m.p. 175 C.

The following compounds can be prepared in an analogous manner:

Butyl 2(R)-[4'-[4-(trans-4-pentylcyclohexyl)-1-butyl]-4-biphenylyloxy]propionate, m.p. (C-S$_B$) 59° C., cl.p. (S$_B$-I) 69° C.;

ethyl 2(R)-[4'-[4-(trans-4-propylcyclohexyl)-1-butyl]-4-biphenylyloxy]propionate;

butyl 2(R)-[4'-[4-(trans-4-pentylcyclohexyl)-1-butyl]-4-biphenylyloxy]propionate.

EXAMPLE 8

Under a nitrogen atmosphere a mixture of 0.46 g of 2-decylmalonaldehyde tetramethyl acetal, 0.02 g of p-toluenesulfonic acid monohydrate and 0.5 ml of water was heated to 70°-80° C. for 30 minutes and then treated with 0.5 g of sodium hydrogen carbonate. The mixture was stirred for a further 5 minutes and then filtered. The filter residue was washed with methanol. The filtrate, containing crude 2-(methoxymethylidene)dodecanal, was added dropwise to 0.4 g of 4-[4-(trans-4-pentylcyclohexyl)-1-butyl]benzamidine hydrochloride, 10 ml of methanol and a sodium methylate solution (prepared from 0.42 ml of methanol and 0.12 g of sodium). The reaction mixture was stirred overnight and subsequently adjusted to pH 3-4 with concentrated hydrochloric acid and extracted three times with 50 ml of dichloromethane each time. The combined organic phases were washed twice with 100 ml of water each time, dried over magnesium sulfate, filtered and subsequently concentrated. The solid residue was purified by chromatography over silica gel with toluene. Recrystallization from ethanol gave 0.4 g of pure 5-decyl-2-[4-[4-(trans-4-pentylcyclohexyl)-1-butyl]phenyl]pyrimidine with m.p. (C-S) 66° C., S-S$_C$ 71° C., S$_C$-S$_A$ 86° C., SA-N 102° C., cl.p. (N-I) 109° C.

The 4-[4-(trans-4-pentylcyclohexyl)-1-butyl]benzamidine hydrochloride used as the starting material was prepared as follows:

a) A solution of 11.6 g of 4-[4-(trans-4-pentylcyclohexyl)-1-butyl]benzonitrile in 7.6 ml of ethanol and 100 ml of toluene was saturated with hydrogen chloride at 0-5° C. and then stirred at room temperature for a further 2 days. Thereafter, the reaction mixture was concentrated, suspended in 300 ml of diethyl ether and then filtered. The filter residue was rinsed with diethyl ether and then dried. This gave 6 g of 4-[4-(trans-4-pentylcyclohexyl)-]butyl]phenyl imidoethyl ether hydrochloride.

b) A solution of 6 g of 4-[4-(trans-4-pentylcyclohexyl)-1-butyl]phenyl imidoethyl ether and 50 ml of ethanol was treated with 11.2 ml of a saturated ethanolic ammonia solution. The reaction mixture was stirred at room temperature for a further 2 days and then concentrated. The solid residue was dissolved in 50 ml of ethanol and then treated with 600 ml of diethyl ether, whereby the product separated as a white, fine precipitate. This precipitate was removed by filtration and dried. This gave 5.2 g of 4-[4-(trans-4-pentylcyclohexyl)-1-butyl]benzamidine hydrochloride.

The following compounds can be prepared in an analogous manner:

5-Pentyl-2-[4-[4-(trans-4-pentylcyclohexyl)-1-butyl]phenyl]pyrimidine, m.p. (C-N) 78° C., cl.p. (N-I) 119° C.;

5-hexyl-2-[4-[4-(trans-4-pentylcyclohexyl)-1-butyl]phenyl]pyrimidine, m.p. (C-N) 79° C., cl.p. (N-I) 113° C.;

5-heptyl-2-[4-[4-(trans-4-pentylcyclohexyl)-1-butyl]phenyl]pyrimidine, m.p. (C-N) 77° C., cl.p. (N-I) 116° C.;

5-octyl-2-[4-[4-(trans-4-pentylcyclohexyl)-1-butyl]phenyl]pyrimidine, m.p. (C-N) 69° C., S$_C$-N 64° C., cl.p. (N-I) 110° C.;

5-nonyl-2-[4-[4-(trans-4-pentylcyclohexyl)-1-butyl]phenyl]pyrimidine, m.p. (C-S$_C$) 74° C., S-S$_C$ 62° C., S$_C$-S$_A$ 82° C., S$_A$-N 97° C., cl.p. (N-I) 113° C.;

5-undecyl-2-[4-[4-(trans-4-pentylcyclohexyl)-1-butyl]phenyl]pyrimidine, m.p. (C-S$_C$) 48° C., S-S$_C$ 71° C., S$_C$-S$_A$ 81° C., S$_A$-N 106° C., cl.p. (N-I) 110° C.;

5-dodecyl-2-[4-[4-(trans-4-pentylcyclohexyl)-1-butyl]phenyl]pyrimidine.

We claim:

1. A compound of formula

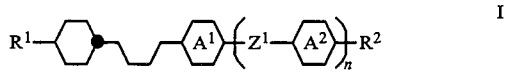

wherein n is 0 or 1: R$^1$ represents a group R$^3$ or R$^3$—A$^3$—Z$^2$—; R$^2$ is a group R$^4$ or R$^4$—A$^4$—Z$^3$—; ring A$^1$ represents 1,4-phenylene or 1,4-phenylene having 1CH or 2CH groups replaced by nitrogen, the rings A$^1$ being unsubstituted or substituted with at least one of halogen, cyano or methyl: A$^3$, A$^4$ and ring A$^2$ each independently represent 1,4-phenylene or 1,4-phenylene having 1CH or 2CH groups replaced by nitrogen, each of the 1,4-phenylene or 1,4-phenylene having 1CH or 2CH groups replaced by nitrogen being unsubstituted or substituted with at least one of halogen, cyano or methyl, or trans-1,4-cyclohexylene, trans-1,3-dioxane-2,5-diyl, 1-cyano-trans-1,4-cyclohexylene, bicyclo [2.2.2]octane-1,4-diyl, naphthalene-2,6-diyl, tetralin-2,6-diyl or and trans-decalin-2,6-diyl; Z$^1$, Z$^2$ and Z$^3$ each independently represent a single covalent bond, —COO—, —OOC—, CH$_2$O—, —OCH$_2$—, —CH$_2$CH$_2$—, —C|C—, —(CH$_2$)$_3$)—, —O(CH$_2$)$_3$—, —(CH$_2$)$_4$— or a trans form of —CH=CH—CH$_2$O— or —OCH$_2$—CH=CH—; R$^3$ and R$^4$ have a maximum of 18 carbon atoms and each independently represent halogen, cyano, —NCS, —CF$_3$, —OCF$_3$, alkyl, alkyl having one >CH—CH< replaced by >C=C<, alkyl having one methylene group or two non-adjacent methylene groups replaced by at least one of —O—, —COO— or —OOC—, alkyl having one methylene group replaced by —CHX—, alkyl with one methylene group or two non-adjacent methylene groups being replaced by at least one of —O—, —COO— or —OOC—, and one methylene group being replaced by —CHX—, alkyl having >CH—CH< replaced by >C=C< with one methylene group or two non-adjacent methylene groups being replaced by at least one of —O—, —COO— or —OOC—, alkyl having one >CH—CH< replaced by >C=C< with one methylene group replaced by —CHX—, and alkyl having one >CH—CH< replaced by >C═C< with one methylene or two non-adjacent methylene groups being replaced by at least one of —O—, —COO— or —OOC—, and one methylene group being replaced by —CHX—; and X represents halogen, cyano or methyl.

2. A compound according to claim 1 of formula

I-1

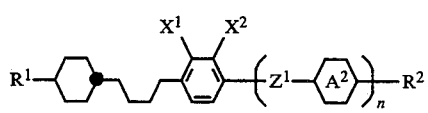

wherein n, $R^1$ $R^2$, $Z^1$ and ring $A^2$ have the significances given in claim 1 and $X^1$ and $X^2$ each independently denote hydrogen, halogen, cyano or methyl.

3. A compound according to claim 1, wherein $A^3$ and $A^4$ each independently represent trans-1,4-cyclohexylene or 1,4-phenylene, the 1,4-phenylene being unsubstituted or substituted with at least one of halogen, cyano or methyl.

4. A compound according to claim 1, wherein ring $A^2$ represents unsubstituted 1,4-phenylene, 1,4-phenylene which is monosubstituted or 2,3-disubstituted with at least one of halogen, cyano or methyl, or trans-1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,6-diyl, trans-decalin-2,6-diyl, pyridine-2,5-diyl, pyrimidine-2,5-diyl or pyrazine-2,5-diyl.

5. A compound according to claim 1, wherein $Z^1$, $Z^2$ and $Z^3$ each are a single covalent bond.

6. A compound according to claim 1, wherein two of the groups $Z^1$, $Z^2$ and $Z^3$ each are a single covalent bond and one of the groups $Z^1$, $Z^2$ and $Z^3$ is —COO—, —OOC—, —CH$_2$O—, —OCH$_2$—, —CH$_2$CH$_2$—, —C|C—, —(CH$_2$)$_3$O—, —O(CH$_2$)$_3$O—, —(CH$_2$)$_4$— or the trans form of —CH═CH—CH$_2$O— or —OCH$_2$—CH═CH.

7. A compound according to claim 1 of formulas

I-7
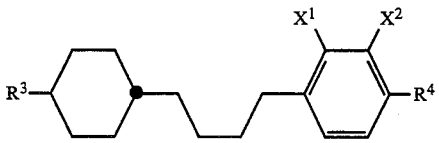

I-8
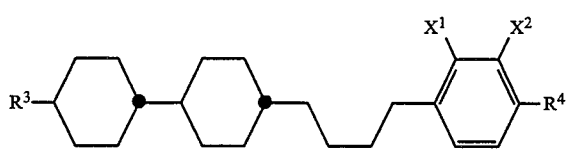

I-9
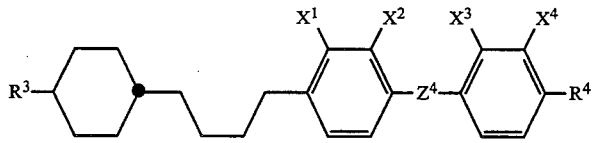

I-10
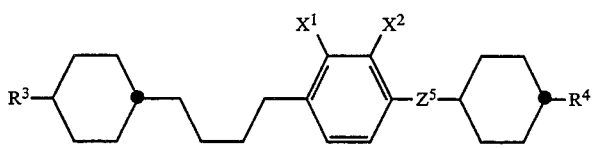

I-11
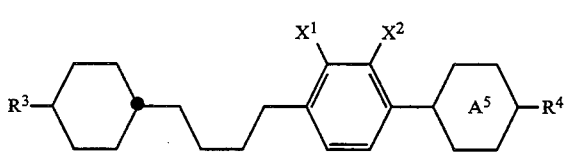

I-12
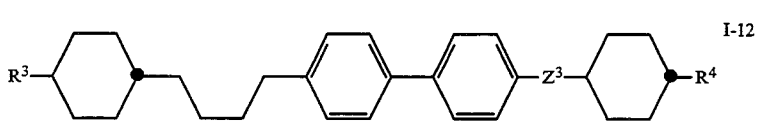

wherein $R^3$, $R^4$ and $Z^3$ have the significances given in claim 1 $X^1$, $X^2$, $X^3$ and $X^4$ each independently denote hydrogen, halogen, cyano or methyl, $Z^4$ is a single covalent bond, —COO—, —OOC— or —C|C—; $Z^5$ denotes a single covalent bond, —OOC—, —OCH$_2$—, —CH$_2$CH$_2$—, —C|C—, —O(CH$_2$)3—, —(CH$_2$)$_4$— or the trans form of —OCH$_2$—CH═CH—; and ring $A^5$ represents pyridine-2,5-diyl, pyrimidine-2,5-diyl, pyrazine-2,5-diyl, trans-1,3-dioxane-2,5-diyl, bicyclo[2.2.2]octane-1,4-diyl, naphthalene-2,6-diyl, tetralin-2,6-diyl or trans-decalin-2,6-diyl.

8. A compound according to claim 2 wherein $X^1$, $X^2$, each independently are hydrogen or fluorine.

9. A compound according to claim 7 wherein $X^1$, $X^2$, $X^3$ and $X^4$ each independently are hydrogen or fluorine.

10. A compound according to claim 1 wherein $R^3$ and $R^4$ each independently denote alkyl, alkyl having one CH—CH< replaced by >C═C<, alkyl having one methylene group or two non-adjacent methylene groups replaced by at least one of —O—, —COO— or —OOC—, alkyl having one methylene group replaced by —CHX—, alkyl having one methylene group or two non-adjacent methylene groups replaced by at least one of —O—, —COO— or —OOC— and having one methylene group replaced by —CHX—, alkyl having one CH—CH< replaced by >C=C< with one methylene group or two non-adjacent methylene groups replaced by at least one of —O—, —COO— or —OOC—, alkyl having one >CH—CH< replaced by >C=C< with one methylene group replaced by —CHX— and alkyl having one >CH—CH< replaced by >C=C< with one methylene group or two non-adjacent methylene groups replaced by at least one of —O—, —COO— or —OOC— and having one methylene group replaced by —CHX—; or R⁴ also can be halogen, cyano, —NCS, —CF₃ or —OCF₃.

11. A compound according to claim 1, wherein R³ and R⁴ each have a maximum of 12 carbon atoms.

12. A compound according to claim 1, wherein R³ is alkyl, alkenyl, alkoxy, alkenyloxy, alkoxycarbonyl, alkenyloxycarbonyl, alkanoyloxy or alkenoyloxy.

13. A compound according to claim 13, wherein R³ is alkyl or alkenyl.

14. A compound according to claim 1, wherein R⁴ is alkyl, alkenyl, alkoxy, alkenyloxy, alkoxycarbonyl, alkenyloxycarbonyl, alkanoyloxy, alkenoyloxy, halogen, cyano, —NCS, —CF₃ or —OCF₃.

15. A liquid crystalline mixture with at least 2 components, wherein at least one component is a compound of formula

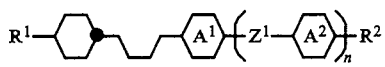

I wherein n is 0 or 1; R¹ represents a group R³ or R³—A³—Z²—; R² is a group R⁴ or R⁴—A⁴—Z³—; ring A¹ represents 1,4-phenylene, or 1,4-phenylene having 1CH or 2CH groups replaced by nitrogen, the rings A¹ being unsubstituted or substituted with at least one of halogen, cyano or methyl; A³, A⁴ and ring A² each independently represent 1,4-phenylene or 1,4-phenylene having 1CH or 2CH groups replaced by nitrogen, each of the 1,4-phenylene or 1,4-phenylene having 1CH or 2CH groups replaced by nitrogen being unsubstituted or substituted with at least one of halogen, cyano or methyl, or trans-1,4-cyclohexylene, trans-1,3-dioxane-2,5-diyl, 1-cyano-trans-1,4-cyclohexylene, bicyclo [2.2.2]octane-1,4-diyl, naphthalene-2,6-diyl, tetralin-2,6-diyl or and trans-decalin-2,6-diyl; Z¹, Z² and Z³ each independently represent a single covalent bond, —COO—, —OOC—, CH₂O—, —OCH₂—, —CH₂CH₂—, —C|—, —(CH₂)₃—, —O(CH₂)₃—, —(CH₂)₄— or a trans form of —CH=CH—CH₂O— or —OCH₂—CH=CH—; R³ and R⁴ have a maximum of 18 carbon atoms and each independently represent halogen, cyano, —NCS, —CF₃, —OCF₃, alkyl, alkyl having one >CH—CH< replaced by >C=C<, alkyl having one methylene group or two non-adjacent methylene groups replaced by at least one of —O—, —COO— or —OOC—, alkyl having one methylene group replaced by —CHX—, alkyl with one methylene group or two non-adjacent methylene groups being replaced by at least one of —O—, —COO—, or —OOC—, and one methylene group being replaced by —CHX—, alkyl having >CH—CH< replaced by >C=C< with one methylene group or two non-adjacent methylene groups being replaced by at least one of —O—, —COO— or —OOC—, alkyl having one >CH—CH< replaced by >C=C< with one methylene group replaced by —CHX—, and alkyl having one >CH—-CH< replaced by >C=C< with one methylene or two non-adjacent methylene groups being replaced by at least one of —O—, —COO— or —OOC—, and one methylene group being replaced by —CHX—; and X represents halogen, cyano or methyl.

16. A liquid crystal cell comprising:
a) two plate means;
b) liquid crystal means disposed between the two plate means and including a compound of formula

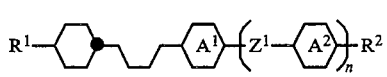

I wherein n is 0 or 1: R¹ represents a group R³ or R³—A³—Z³—; R² is a group R⁴ or R⁴—A⁴—Z³—; ring A¹ represents 1,4-phenylene, or 1,4-phenylene having 1CH or 2CH groups replaced by nitrogen, the rings A¹ being unsubstituted or substituted with at least one of halogen, cyano or methyl; A³, A⁴ and ring A² each independently represent 1,4-phenylene or 1,4-phenylene having 1CH or 2CH groups replaced by nitrogen, each of the 1,4-phenylene or 1,4-phenylene having 1CH or 2CH groups replaced by nitrogen being unsubstituted or substituted with at least one of halogen, cyano or methyl, or trans-1,4-cyclohexylene, trans-1,3-dioxane-2,5-diyl, 1-cyano-trans-1,4-cyclohexylene, bicyclo [2.2.2]octane-1,4-diyl, naphthalene-2,6-diyl, tetralin-2,6-diyl or and trans-decalin-2,6-diyl; Z¹, Z² and Z³ each independently represent a single covalent bond, —COO—, —OOC—, CH₂O—, —OCH₂—, —CH₂CH₂—, —C|C—, —(CH₂)₃—, —O(CH₂)₃—, —(CH₂)₄— or a trans form of —CH=CH—CH₂O— or —OCH₂—CH=CH—; R³ and R⁴ have a maximum of 18 carbon atoms each independently represent halogen, cyano, —NCS, —CF₃, —OC₃, alkyl, alkyl having one >CH—CH< replaced by >C=C<, alkyl having one methylene group or two non-adjacent methylene groups replaced by at least one of —O—, —COO— or —OOC—, alkyl having one methylene group replaced by —CHX—, alkyl with one methylene group or two non-adjacent methylene groups being replaced by at least one of —O—, —COO— or —OOC—, and one methylene group being replaced by —CHX—, alkyl having >CH—CH replaced by >C=C< with one methylene group or two non-adjacent methylene groups being replaced by at least one of —O—, —COO— or —OOC—, alkyl having one >CH—CH< replaced by >C=C< with one methylene group replaced by —CHX—, and alkyl having one >CH—CH< replaced by >C=C< with one methylene or two non-adjacent methylene groups being replaced by at least one of —O—, —COO— or —OOC—, and one methylene group being replaced by —CHX—; and X represents halogen, cyano or methyl; and c) means for applying an electrical potential to said plate means.

17. A compound of claim 1 of the formula:

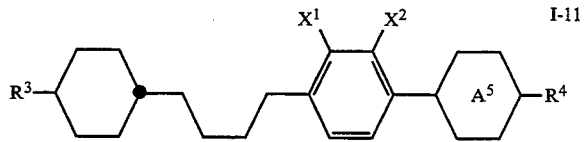

wherein R³ and R⁴ have a maximum of 18 carbon atoms and each independently represent halogen, cyano, —NCS, —CF₃, —OCF₃, alkyl, alkyl having one >CH—CH< replaced by >C=C<, alkyl having one methylene group or two non-adjacent methylene groups replaced by at least one of —O—, —COO— or —OOC, alkyl having one methylene group replaced by —CHX—, alkyl with one methylene group or two non-adjacent methylene groups being replaced by at least one of —O—, —COO— or —OOC, and one methylene group being replaced by —CHX—, alkyl having >CH—< replaced by >C=< with one methylene group or two non-adjacent methylene groups being replaced by at least one of —O—, —COO— or —OOC, alkyl, having one >CH—CH< replaced by >C=C< with one methylene group replaced by —CHX—, and alkyl having one >CH—CH< replaced by >C=C— with one methylene or two non-adjacent methylene groups being replaced by at least one of —O—, —COO— or —OOC, and one methylene group being replaced by —CHX—; and X represents halogen, cyano or methyl; X¹ and X² each independently denote hydrogen, halogen, cyano or methyl; and ring A⁵ represents pyridine-2,5-diyl, pyrimidine-2,5-diyl, and pyrazine-2,5-diyl.

18. A compound of claim 18 of the formula

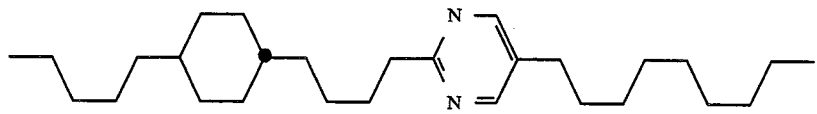

* * * * *

UNITED STATES PATENT AND TRADEMARK OFFICE
CERTIFICATE OF CORRECTION

PATENT NO. : 5,346,647

DATED : September 13, 1994

INVENTOR(S) : Stephen Kelly and Frans Leenhouts

It is certified that error appears in the above-indentified patent and that said Letters Patent is hereby corrected as shown below:

Column 28, Claim 1, Line 51;

Column 31, Claim 15, Line 52; and

Column 32, Claim 16, Line 38,

Change "-C/C-, -(CH$_2$)$_3$)-," to -- -C≡C-, -(CH$_2$)$_3$O-, --

Column 30, Claim 6, Line 7; and

Column 30, Claim 7, Lines 51 and 53,

Change "-C/C-" to -- -C≡C- --

UNITED STATES PATENT AND TRADEMARK OFFICE
CERTIFICATE OF CORRECTION

PATENT NO. : 5,346,647
DATED : September 13, 1994
INVENTOR(S) : Stephen Kelly and Frans Leenhouts It is certified that error appears in the above-indentified patent and that said Letters Patent is hereby corrected as shown below:

Column 30, Claim 10, Line 65; and

Column 31, Claim 10, Line 5,

Change "CH-CH<" to  -- >CH-CH< --

Column 31, Claim 13, Line 21,

Change "according to claim 13" to -- according to claim 12 --.

Column 32, Claim 16, Line 20, first instance,

Change "$Z^3$" to -- $Z^2$ --.

UNITED STATES PATENT AND TRADEMARK OFFICE
CERTIFICATE OF CORRECTION

PATENT NO. : 5,346,647
DATED : September 13, 1994
INVENTOR(S) : Stephen Kelly and Frans Leenhouts It is certified that error appears in the above-indentified patent and that said Letters Patent is hereby corrected as shown below:

Column 34, Claim 17, Line 2

Change ">CH-<" to -- >CH-CH< -- and

">C=<" to -- >C=C< --.

Column 34, Claim 17, Line 7

Change ">C=C-" to -- >C=C< --

Signed and Sealed this

Eleventh Day of July, 1995

Attest:

BRUCE LEHMAN

Attesting Officer

Commissioner of Patents and Trademarks